United States Patent
Otsuka et al.

(10) Patent No.: US 10,241,025 B2
(45) Date of Patent: Mar. 26, 2019

(54) MICROPARTICLE SORTING DEVICE, AND METHOD AND PROGRAM FOR SORTING MICROPARTICLES

(71) Applicant: Sony Corporation, Tokyo (JP)

(72) Inventors: Fumitaka Otsuka, Tokyo (JP); Yosuke Muraki, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 15/687,948

(22) Filed: Aug. 28, 2017

(65) Prior Publication Data

US 2018/0058999 A1 Mar. 1, 2018

Related U.S. Application Data

(63) Continuation of application No. 14/386,368, filed as application No. PCT/JP2013/081152 on Nov. 19, 2013, now Pat. No. 9,784,660.

(30) Foreign Application Priority Data

Jan. 28, 2013 (JP) ................. 2013-013801
Jun. 12, 2013 (JP) ................. 2013-124209

(51) Int. Cl.
*G01N 15/14* (2006.01)
*B07C 5/342* (2006.01)
(Continued)

(52) U.S. Cl.
CPC ....... *G01N 15/1425* (2013.01); *B07C 5/3422* (2013.01); *G01N 15/1427* (2013.01);
(Continued)

(58) Field of Classification Search
None
See application file for complete search history.

(56) References Cited

U.S. PATENT DOCUMENTS 3,710,933 A 1/1973 Fulwyler et al.
3,826,364 A 7/1974 Bonner et al.
(Continued)

FOREIGN PATENT DOCUMENTS

CN 1950690 A 4/2007
EP 1403633 A2 3/2004
(Continued)

OTHER PUBLICATIONS

U.S. Appl. No. 13/788,075, filed Mar. 7, 2013, Muraki et al.
(Continued)

*Primary Examiner* — Prasad V Gokhale
(74) *Attorney, Agent, or Firm* — Wolf, Greenfield & Sacks, P.C.

(57) ABSTRACT

Provided are a microparticle sorting device, and a method and a program for sorting microparticles capable of stabilizing sorting performance over a prolonged period of time. The microparticle sorting device includes an imaging element and a controller. The imaging element obtains an image of fluid and fluid droplets at a position where the fluid discharged from an orifice which generates a fluid stream is converted into the fluid droplets. The controller controls driving voltage of an oscillation element which gives oscillation to the orifice and/or controls a position of the imaging element based on a state of the fluid in the image and/or a state of a satellite fluid droplet. The satellite fluid droplet does not include microparticles and exists between the position, where the fluid is converted into the fluid droplets, and a fluid droplet, among fluid droplets including the microparticles, which is closest to the position where the fluid is converted into the fluid droplets.

2 Claims, 12 Drawing Sheets

(51) Int. Cl.
*G01N 21/27* (2006.01)
*G01N 15/10* (2006.01)

(52) U.S. Cl.
CPC ..... *G01N 15/1459* (2013.01); *G01N 15/1463* (2013.01); *G01N 21/27* (2013.01); *G01N 2015/1006* (2013.01); *G01N 2015/1406* (2013.01); *G01N 2015/149* (2013.01); *G01N 2015/1481* (2013.01)

(56) References Cited

U.S. PATENT DOCUMENTS

| | | |
|---|---|---|
| 3,924,947 A | 12/1975 | Hogg |
| 4,009,435 A | 2/1977 | Hogg |
| 4,168,460 A | 9/1979 | Menke |
| 4,173,415 A | 11/1979 | Wyatt |
| 4,284,496 A | 8/1981 | Newton |
| 4,318,480 A | 3/1982 | Lombardo et al. |
| 4,318,481 A | 3/1982 | Lombardo et al. |
| 4,325,483 A | 4/1982 | Lombardo et al. |
| 4,538,733 A | 9/1985 | Hoffman |
| 4,616,234 A | 10/1986 | Wint |
| 4,987,539 A | 1/1991 | Moore et al. |
| 5,080,770 A | 1/1992 | Culkin |
| 5,180,065 A | 1/1993 | Touge et al. |
| 5,483,469 A | 1/1996 | Van den Engh et al. |
| 5,602,039 A | 2/1997 | Van den Engh |
| 5,700,692 A * | 12/1997 | Sweet ................ G01N 15/1404 209/577 |
| 5,776,781 A | 7/1998 | Vardanega et al. |
| 6,079,836 A | 6/2000 | Burr et al. |
| 6,202,734 B1 | 3/2001 | Sackinger et al. |
| 6,248,590 B1 | 6/2001 | Malachowski |
| 6,372,506 B1 * | 4/2002 | Norton ............... G01N 15/1404 209/127.4 |
| 6,410,872 B2 | 6/2002 | Campbell et al. |
| 6,589,792 B1 | 7/2003 | Malachowski |
| 6,861,265 B1 | 3/2005 | den Engh |
| 6,941,005 B2 * | 9/2005 | Lary ................ G01N 15/1425 356/317 |
| 6,949,715 B2 | 9/2005 | Kelly |
| 7,019,293 B1 | 3/2006 | Hamada |
| 7,024,316 B1 | 4/2006 | Ellison et al. |
| 7,159,752 B2 | 1/2007 | Farnworth |
| 7,417,734 B2 * | 8/2008 | Kanda ................ G01N 15/1459 356/337 |
| 7,639,358 B2 | 12/2009 | Kanda |
| 7,691,636 B2 | 4/2010 | Frazier et al. |
| 7,758,811 B2 | 7/2010 | Durack et al. |
| 7,880,108 B2 | 2/2011 | Schembri et al. |
| 7,901,947 B2 | 3/2011 | Pollack et al. |
| 8,246,805 B2 | 8/2012 | Shinoda |
| 8,570,511 B2 | 10/2013 | Wang |
| 8,681,335 B2 | 3/2014 | Sharpe et al. |
| 8,748,183 B2 | 6/2014 | Durack et al. |
| 8,883,513 B2 | 11/2014 | Pollack et al. |
| 8,922,636 B1 | 12/2014 | Belden et al. |
| 8,922,646 B2 * | 12/2014 | Neckels ............ G01N 15/1427 348/135 |
| 9,029,724 B2 | 5/2015 | Hashimoto et al. |
| 9,087,371 B2 | 7/2015 | Muraki |
| 9,339,823 B2 | 5/2016 | Muraki et al. |
| 9,429,276 B2 | 8/2016 | Katsumoto |
| 9,588,036 B2 | 3/2017 | Shinoda |
| 9,784,659 B2 | 10/2017 | Tanase et al. |
| 9,784,660 B2 | 10/2017 | Otsuka et al. |
| 9,857,286 B2 | 1/2018 | Muraki et al. |
| 9,915,599 B2 | 3/2018 | Brun et al. |
| 9,915,935 B2 | 3/2018 | Muraki et al. |
| 9,958,375 B2 | 5/2018 | Muraki et al. |
| 2002/0171827 A1 | 11/2002 | van ven Engh |
| 2003/0222950 A1 | 12/2003 | Jeanmaire |
| 2004/0062685 A1 | 4/2004 | Norton et al. |
| 2004/0086159 A1 * | 5/2004 | Lary ................ G01N 15/1425 382/128 |
| 2006/0125856 A1 | 6/2006 | Kitami et al. |
| 2006/0177348 A1 | 8/2006 | Yasuda et al. |
| 2007/0102634 A1 | 5/2007 | Frey et al. |
| 2007/0195310 A1 * | 8/2007 | Kanda ................ G01N 15/1459 356/73 |
| 2007/0257215 A1 | 11/2007 | Rich |
| 2008/0024619 A1 | 1/2008 | Ono |
| 2008/0050283 A1 | 2/2008 | Chou et al. |
| 2008/0053205 A1 | 3/2008 | Pollack et al. |
| 2008/0067068 A1 | 3/2008 | Li |
| 2008/0092655 A1 | 4/2008 | Takiguchi |
| 2008/0255705 A1 | 10/2008 | Degeal et al. |
| 2008/0284827 A1 | 11/2008 | Fagerquist et al. |
| 2008/0289966 A1 | 11/2008 | Voldman et al. |
| 2009/0125242 A1 | 5/2009 | Choi et al. |
| 2009/0170186 A1 | 7/2009 | Wu et al. |
| 2010/0009445 A1 | 1/2010 | Patra et al. |
| 2010/0118300 A1 | 5/2010 | Wang et al. |
| 2010/0315639 A1 | 12/2010 | Muraki |
| 2011/0005931 A1 | 1/2011 | Zhe et al. |
| 2011/0033339 A1 | 2/2011 | Muraki |
| 2011/0081684 A1 | 4/2011 | Gauer et al. |
| 2011/0221892 A1 * | 9/2011 | Neckels ............ G01N 15/1427 348/135 |
| 2011/0259749 A1 | 10/2011 | Kanda |
| 2011/0267457 A1 | 11/2011 | Weitz et al. |
| 2011/0275052 A1 | 11/2011 | Schenk et al. |
| 2011/0284378 A1 | 11/2011 | Shinoda |
| 2011/0287976 A1 | 11/2011 | Wang et al. |
| 2012/0076349 A1 | 3/2012 | Manri et al. |
| 2012/0084022 A1 | 4/2012 | Giovangrandi et al. |
| 2012/0135874 A1 | 5/2012 | Wang et al. |
| 2012/0200857 A1 | 8/2012 | Sharpe et al. |
| 2012/0202237 A1 | 8/2012 | Sedoglavich et al. |
| 2012/0247231 A1 | 10/2012 | Kery et al. |
| 2012/0301869 A1 | 11/2012 | Evans |
| 2012/0314096 A1 | 12/2012 | Kruglick |
| 2013/0188040 A1 | 7/2013 | Kamen et al. |
| 2013/0194589 A1 | 8/2013 | Suzuki |
| 2013/0256136 A1 * | 10/2013 | Muraki .................. B03C 7/003 204/555 |
| 2013/0256197 A1 | 10/2013 | Katsumoto |
| 2013/0258075 A1 | 10/2013 | Muraki et al. |
| 2014/0021370 A1 | 1/2014 | Suzuki et al. |
| 2014/0043436 A1 | 2/2014 | Bell et al. |
| 2014/0087453 A1 | 3/2014 | Tahara |
| 2014/0097129 A1 | 4/2014 | Foster et al. |
| 2014/0144817 A1 | 5/2014 | Hashimoto et al. |
| 2014/0174206 A1 | 6/2014 | Akiyama et al. |
| 2014/0193059 A1 * | 7/2014 | Muraki ............. G01N 15/1484 382/133 |
| 2014/0208875 A1 | 7/2014 | Muraki |
| 2014/0212917 A1 * | 7/2014 | Durack ............ G01N 15/1427 435/34 |
| 2014/0346047 A1 | 11/2014 | Shinoda |
| 2014/0354795 A1 | 12/2014 | Tracy et al. |
| 2015/0057787 A1 | 2/2015 | Muraki et al. |
| 2015/0068957 A1 | 3/2015 | Otsuka et al. |
| 2015/0204774 A1 | 7/2015 | Ito |
| 2015/0285726 A1 | 10/2015 | Tanase et al. |
| 2015/0285727 A1 * | 10/2015 | Muraki ............. G01N 15/1484 209/3.1 |
| 2015/0377763 A1 | 12/2015 | Brun et al. |
| 2016/0148433 A1 | 5/2016 | Petrovskaya et al. |
| 2016/0223451 A1 | 8/2016 | Muraki et al. |
| 2016/0245736 A1 | 8/2016 | Muraki et al. |
| 2016/0266027 A1 | 9/2016 | Muraki et al. |
| 2017/0191925 A1 | 7/2017 | Otsuka et al. |
| 2017/0241889 A1 | 8/2017 | Otsuka et al. |
| 2018/0188150 A1 | 7/2018 | Muraki et al. |

FOREIGN PATENT DOCUMENTS

| | | |
|---|---|---|
| GB | 1 103 190 A | 2/1968 |
| JP | 53-013263 | 2/1978 |
| JP | 56-030870 A | 3/1981 |
| JP | 62-036542 A | 2/1987 |
| JP | 62-167478 A | 7/1987 |

(56) References Cited

FOREIGN PATENT DOCUMENTS

| JP | 64-012245 A | 1/1989 |
|---|---|---|
| JP | 09-189653 A | 7/1997 |
| JP | 10-507525 A | 7/1998 |
| JP | 11-501258 A | 2/1999 |
| JP | 2002-505423 A | 2/2002 |
| JP | 2002-521658 A | 7/2002 |
| JP | 2004-257756 A | 9/2004 |
| JP | 2005-315799 A | 11/2005 |
| JP | 2006-504970 A | 2/2006 |
| JP | 2006-242849 A | 9/2006 |
| JP | 2006-292769 A | 10/2006 |
| JP | 2007-532874 A | 11/2007 |
| JP | 2008-107110 A | 5/2008 |
| JP | 2009-145213 A | 7/2009 |
| JP | 2009-198511 A | 9/2009 |
| JP | 2009-298012 A | 12/2009 |
| JP | 2010-510782 A | 4/2010 |
| JP | 2010-190680 A | 9/2010 |
| JP | 2010-216992 A | 9/2010 |
| JP | 2010-286292 A | 12/2010 |
| JP | 2010-286341 A | 12/2010 |
| JP | 2011-033598 A | 2/2011 |
| JP | 4805417 B1 | 2/2011 |
| JP | 2011-509075 A | 3/2011 |
| JP | 2011-232033 A | 11/2011 |
| JP | 2011-237201 A | 11/2011 |
| JP | 2012-047464 A | 3/2012 |
| JP | 2013-210264 A | 10/2013 |
| JP | 2013-210270 A | 10/2013 |
| JP | 2015-152439 A | 8/2015 |
| WO | WO 2001/002836 A1 | 1/2001 |
| WO | WO 2010/095391 A1 | 8/2010 |
| WO | WO 2010/129787 A1 | 11/2010 |
| WO | WO 2010/140460 A1 | 12/2010 |
| WO | WO 2013/145905 A1 | 10/2013 |
| WO | WO 2014/115409 A1 | 7/2014 |

OTHER PUBLICATIONS

U.S. Appl. No. 13/788,165, filed Mar. 7, 2013, Muraki et al.
U.S. Appl. No. 14/026,023, filed Sep. 13, 2013, Tahara.
U.S. Appl. No. 14/118,788, filed Nov. 19, 2013, Muraki.
U.S. Appl. No. 14/118,994, filed Nov. 20, 2013, Hashimoto et al.
U.S. Appl. No. 14/239,794, filed Feb. 20, 2014, Muraki.
U.S. Appl. No. 14/386,368, filed Sep. 19, 2014, Otsuka et al.
U.S. Appl. No. 14/386,499, filed Sep. 19, 2014, Muraki et al.
U.S. Appl. No. 14/413,543, filed Jan. 8, 2015, Ito.
U.S. Appl. No. 14/440,765, filed May 5, 2015, Tanase et al.
U.S. Appl. No. 14/737,370, filed Jun. 11, 2015, Muraki.
U.S. Appl. No. 14/763,980, filed Jul. 28, 2015, Brun et al.
U.S. Appl. No. 15/028,411, filed Apr. 8, 2016, Muraki et al.
U.S. Appl. No. 15/028,419, filed Apr. 8, 2016, Muraki et al.
U.S. Appl. No. 15/093,879, filed Apr. 8, 2016, Muraki et al.
International Search Report and Written Opinion dated Jan. 8, 2015 in connection with International Application No. PCT/JP2014/005167.
International Preliminary Report on Patentability dated Apr. 28, 2016 in connection with International Application No. PCT/JP2014/005167.
International Search Report and Written Opinion and English translation thereof dated Nov. 18, 2014 in connection with International Application No. PCT/JP2014/074610.
International Preliminary Report on Patentability and English translation thereof dated Apr. 28, 2016 in connection with International Application No. PCT/JP2014/074610.
International Search Report and English translation thereof dated Sep. 27, 2016 in connection with International Application No. PCT/JP2016/070938.
International Search Report and Written Opinion dated Nov. 6, 2015 in connection with International Application No. PCT/JP2015/004282.
International Preliminary Report on Patentability dated Mar. 16, 2017 in connection with International Application No. PCT/JP2015/004282.
International Search Report and Written Opinion and English translation thereof dated Feb. 24, 2015 in connection with International Application No. PCT/JP2014/080588.
Japanese Office Action and English translation thereof dated Dec. 15, 2015 in connection with Japanese Application No. 2012-080366.
Chinese Office Action and English translation thereof dated Mar. 3, 2016 in connection with Chinese Application No. 2013100954250.
International Search Report and Written Opinion dated Mar. 11, 2014 in connection with International Application No. PCT/JP2013/005910.
International Preliminary Report on Patentability dated May 21, 2015 in connection with International Application No. PCT/JP2013/005910.
Japanese Office Action dated Feb. 23, 2016 in connection with Japanese Application No. 2012-246432 and English translation thereof.
International Search Report and English translation thereof dated Mar. 12, 2013 in connection with Application No. PCT/JP2013/053324.
International Preliminary Report on Patentability and English translation thereof dated Oct. 9, 2014 in connection with Application No. PCT/JP2013/053324.
Extended European Search Report dated Aug. 26, 2014 in connection with Application No. 13768656.4.
International Search Report and Written Opinion and English translation thereof dated Mar. 5, 2013 in connection with Application No. PCT/JP2013/052467.
Japanese Office Action dated Jul. 15, 2014 and English translation thereof in connection with Application No. 2013-547043.
International Search Report and Written Opinion and English translation thereof dated Jan. 21, 2014 in connection with Application No. PCT/JP2013/081152.
International Preliminary Report on Patentability and English translation thereof dated Aug. 6, 2015 in connection with Application No. PCT/JP2013/081152.
International Preliminary Report on Patentability and English translation thereof dated Aug. 25, 2016 in connection with International Application No. PCT/JP2014/080588.
Bonner et al., Flourescence Activated Cell Sorting. Review of Scientific Instruments. Mar. 1972; 43(3):404-9.
McIntyre et all., Quantitative SLM-based differential interference contrast imaging. Optics Express. Jun. 2010; 18(13):14063-78.
No Author Listed, Differential Interference Contrast, Olympus Microscopy Resource Center, https://web.archive.org/web/20160510073659/http://www.olympusmicro.com:80/primer/techniques/dic/dichome.html, retrieved from the WayBack Machine on Mar. 22, 2018, noting date of May 10, 2016, 2 pages.
No Author Listed, The EPICS® ALTRA™ Flow Cytometer, Sorting Tutorial, Jul. 1, 2000, Coulter International Corporation, 47 pages.
Shapiro, HM, Chapter 6: Flow Sorting, Practical Flow Cytometry, 4th Edition, Dec. 31, 2003, pp. 257-271.
Yoshimura et al., The Latest Technology [Modern Technology] of a Cell Sorter, Applied Research Report, Jasco Report. 1990;32(1):1-20.
Hartman et al., Jet break-up in electrohydrodynamic atomization in the cone-jet mode. J. Aerosol Sci. vol. 31(1), pp. 65-95; Mar. 1999.
Orme et al., Electrostatic charging and deflection of nonconventional droplet streams formed from capillary stream breakup. Phys. Fluids. vol. 12(9); Sep. 2000; pp. 2224-2235.
International Preliminary Report on Patentability and English translation thereof dated May 3, 2018 in connection with International Application No. PCT/JP2016/070938.
Written Opinion and English translation thereof dated Sep. 27, 2016 in connection with International Application No. PCT/JP2016/070938.
Murphy et al., Differential Interference Contrast, Olympus Microscopy Resource Center, https://web.archive.org/web/20030312041453/http://www.olympusmicro.com:80/primer/techniques/dic/dichome.

(56) References Cited

OTHER PUBLICATIONS html, retrieved from the WayBack Machine on Mar. 30, 2018, noting date of Mar. 12, 2003, 3 pages.

Yoon et al., 3D particle position and 3D velocity field measurement in microvolume via the defocusing concept. Meas. Sci. Technol. 17 (2006) 2897-2905.

Morton et al., Hydrodynamic metamaterials: Microfabricated arrays to steer, refract, and focus streams of biomaterials. PNAS May 27, 2008. vol. 105(21); 7434-7438.

Luo et al., Three-dimensional tracking of fluorescent particles applied to micro-fluidic measurements. 2006. J. Micromech. Microeng. vol. 16; 1689-1699.

\* cited by examiner

DRIVING VOLTAGE $V_2$
($V_2 < V_3 < V_4$)

DRIVING VOLTAGE $V_3$
($V_2 < V_3 < V_4$)

DRIVING VOLTAGE $V_4$
($V_2 < V_3 < V_4$)

FLUID DROPLET
STABLE STATE
(DRIVING VOLTAGE $V_5$)

FLUID DROPLET UNSTABLE
STATE DUE TO OBSTRUCTIONS
AND BUBBLES
(DRIVING VOLTAGE $V_5$)

*FIG. 9A* *FIG. 9B*
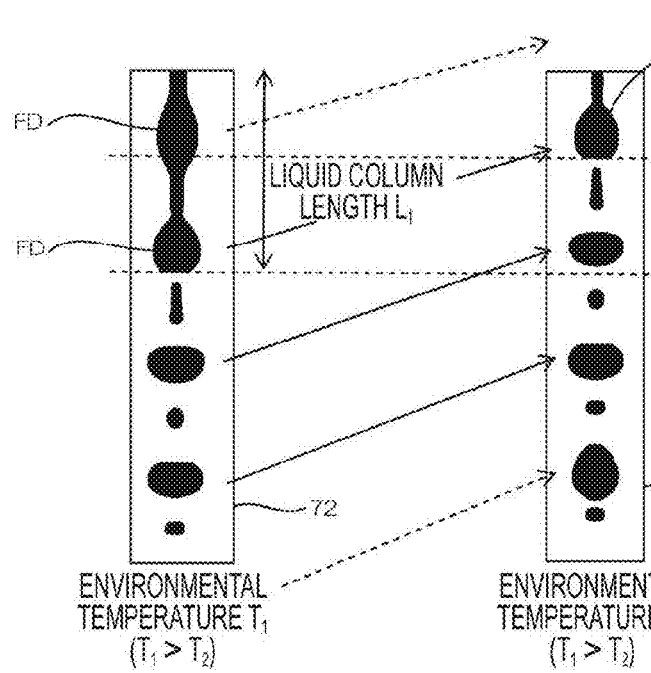
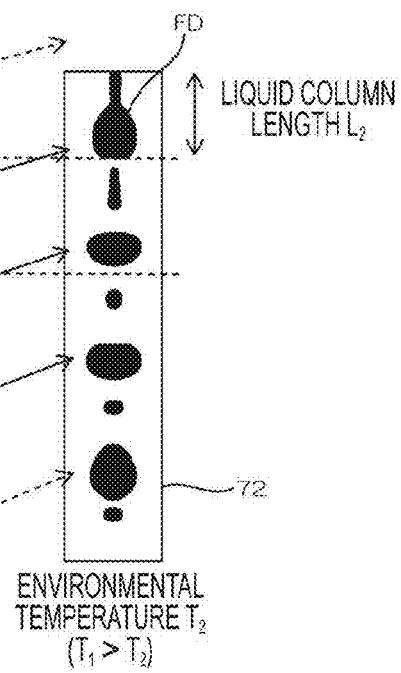
*FIG. 10A* *FIG. 10B*
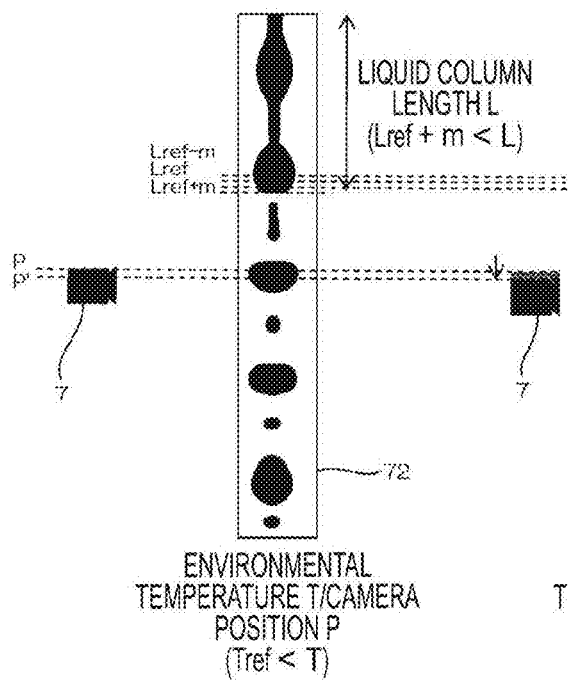
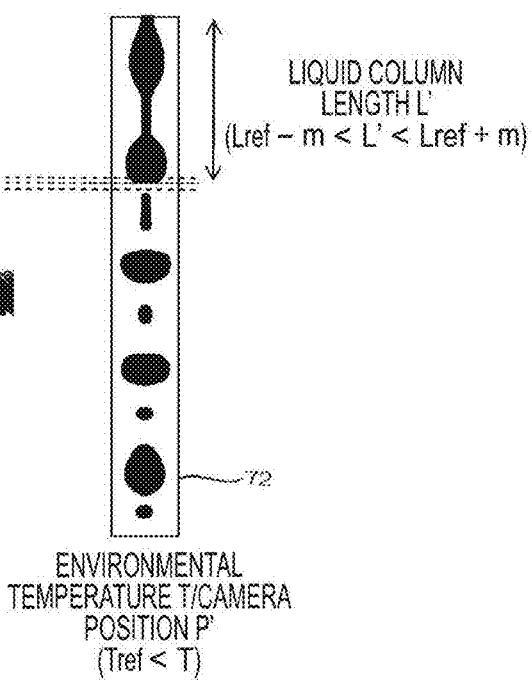

SHEATH PRESSURE P₁
(P₁ < P₂)

SHEATH PRESSURE P₂
(P₁ < P₂)

MICROPARTICLE SORTING DEVICE, AND METHOD AND PROGRAM FOR SORTING MICROPARTICLES

CROSS REFERENCES TO RELATED APPLICATIONS

This application is a continuation of and claims the benefit under 35 U.S.C. § 120 of U.S. patent application Ser. No. 14/386,368, titled "MICROPARTICLE SORTING DEVICE, AND METHOD AND PROGRAM FOR SORTING MICROPARTICLES," filed on Sep. 19, 2014, which is the National Stage of International Application No. PCT/JP2013/081152, filed in the Japanese Patent Office as a Receiving Office on Nov. 19, 2013, which claims priority to Japanese Patent Application No. JP 2013-124209, filed in the Japanese Patent Office on Jun. 12, 2013, and Japanese Patent Application No. 2013-013801, filed Jan. 28, 2013, which are hereby incorporated by reference in their entirety.

TECHNICAL FIELD

The present technology relates to a microparticle sorting device, and a method and a program for sorting microparticles. More specifically, the present technology relates to technology which sorts and recovers microparticles based on results analyzed by an optical method and the like.

BACKGROUND ART

In the related art, an optical measuring method using a flow cytometry (flow cytometer) has been employed to analyze cells, microorganisms, and biologically-relevant microparticles such a liposome. The flow cytometer is a device which irradiates microparticles, which flow through a flow path disposed in a flow cell or a microchip, with light. The flow cytometer also detects fluorescence or scattered light emitted from an individual microparticle, and analyzes the fluorescence or the scattered light.

Examples of the flow cytometer include a device having a function of sorting and recovering, based on the analyzed results, only microparticles which have specific characteristics. Especially, a device which targets a cell as an object to be sorted is called a "cell sorter". Generally, in this cell sorter, fluid discharged from the flow path is converted into fluid droplets by giving oscillation to the flow cell or the microchip with an oscillation element and the like (see Patent Documents 1, 2). The fluid droplets isolated from the fluid are charged with positive (+) or negative (−) charges. Then, traveling directions of the fluid droplets are changed by a deflection plate. After that, the fluid droplets are recovered and put into a predetermined container and the like.

Further, a method has been suggested in the related art as technology for stabilizing sorting performance (see Patent Document 3). In this method, images of fluid or fluid droplets, which are discharged from an outlet nozzle of a flow cell, are taken. Herein, conditions such as pressure including sheath pressure, and crystal drive are adjusted depending on deviations calculated from the images.

CITATION LIST

Patent Documents

Patent Document 1: Japanese PCT National Publication No. 2007-532874

Patent Document 2: Japanese Patent Application Laid-Open No. 2010-190680

Patent Document 3: Japanese PCT National Publication No. 2006-504970

SUMMARY OF INVENTION

Problems to be Solved by the Invention

However, in the above-mentioned microparticle sorting device in the related art, there is a problem that sorting performance may be unstable because of an influence of differential pressure due to changes in temperature, in fluid pressure, and in sheath pressure. This problem can be improved to some extent by taking images of fluid or fluid droplets and adjusting various conditions based on the images, as the technology recited in Patent Document 3. However, in such a case, processes become complicated, and at the same time, errors may easily occur in each process. Such errors include, for example, a sensing error and an error during a change in setting pressure.

Therefore, a primary object of the present disclosure is to provide a microparticle sorting device, and a method and a program for sorting microparticles capable of stabilizing sorting performance over a prolonged period of time.

Solutions to Problems

A microparticle sorting device according to the present disclosure includes: an imaging element configured to obtain an image of fluid and fluid droplets at a position where the fluid discharged from an orifice which generates a fluid stream is converted into the fluid droplets; and a controller configured to control driving voltage of an oscillation element which gives oscillation to the orifice and/or control a position of the imaging element, based on a state of the fluid in the image and/or a state of a satellite fluid droplet which does not include microparticles and exists between the position, where the fluid is converted into the fluid droplets, and a fluid droplet, among fluid droplets including the microparticles, which is closest to the position where the fluid is converted into the fluid droplets.

The controller controls, for example, the driving voltage so that a distance from a position, where the fluid is converted into the fluid droplets, to the satellite fluid droplet and/or a state of a constricted region of the fluid right before being converted into the fluid droplets become constant.

In cases where the state of the constricted region is controlled to be constant, the controller may control the driving voltage so that a width of the constricted region becomes constant.

The controller can further control the driving voltage so that a distance from the position, where the fluid is converted into the fluid droplets, to the narrowest part of the constricted region of the fluid right before being converted into the fluid droplets becomes constant.

Moreover, the controller can also control the position of the imaging element so that the position, in the image, where the fluid is converted into the fluid droplets becomes constant.

In such a case, the controller may calculate a distance from an upper end of the image to the position where the fluid is converted into the fluid droplets. The controller may further control the position of the imaging element so that the distance becomes constant.

On the other hand, this microparticle sorting device may include a sheath liquid storage tank, a first water depth detector, a first pressure detector, and a first pressure controller. The sheath liquid storage tank stores sheath liquid included in the fluid stream. The first water depth detector detects a water depth of the sheath liquid stored in the sheath liquid storage tank. The first pressure detector detects air pressure inside the sheath liquid storage tank. The first pressure controller controls the air pressure inside the sheath liquid storage tank so that a sum of fluid pressure calculated from the water depth detected by the first water depth detector and the air pressure detected by the first pressure detector becomes constant.

The microparticle sorting device herein may further include a sample liquid storage tank, a second water depth detector, a second pressure detector, and a second pressure controller. The sample liquid storage tank stores sample liquid including microparticles and included in the fluid stream. The second water depth detector detects a water depth of the sample liquid stored in the sample liquid storage tank. The second pressure detector detects air pressure inside the sample liquid storage tank. The second pressure controller controls the air pressure inside the sample liquid storage tank so that a sum of the fluid pressure calculated from the water depth detected by the second water depth detector and the air pressure detected by the second pressure detector becomes constant.

In a method for sorting microparticles according to the present disclosure, the driving voltage of the oscillation element which gives oscillation to the orifice and/or the position of the imaging element which obtains the image are controlled, based on the state of the fluid in the image taken at the position where the fluid discharged from the orifice which generates the fluid stream is converted into the fluid droplets and/or the state of the satellite fluid droplet which does not include microparticles and exists between the position, where the fluid is converted into the fluid droplets, and the fluid droplet, among the fluid droplets including the microparticles, which is closest to the position where the fluid is converted into the fluid droplets.

A program according to the present disclosure causes the controller of the microparticle sorting device to execute a function of controlling the driving voltage of the oscillation element which gives oscillation to the orifice and/or the position of the imaging element which obtains the image, based on the state in the image taken at the position where the fluid discharged from the orifice which generates the fluid stream is converted into the fluid droplets and/or the state of the satellite fluid droplet which does not include microparticles and exists between the position, where the fluid is converted into the fluid droplets, and the fluid droplet, among the fluid droplets including the microparticles, which is closest to the position where the fluid is converted into the fluid droplets.

Effects of the Invention

According to the present disclosure, sorting performance can be stabilized over a prolonged period of time.

BRIEF DESCRIPTION OF DRAWINGS

FIGS. 9A and 9B are views showing a status change in a fluid stream due to a change in environmental temperature.
FIGS. 10A and 10B are views showing a method for moving a position of the camera 7 as a position of a break-off point changes.

MODES FOR CARRYING OUT THE INVENTION

Hereinafter, modes for carrying out the present disclosure will be described in detail with reference to the accompanying drawings. Note that the present disclosure is not restricted to each embodiment hereinafter described. Further, the embodiments will be described in the following order.
1. First Embodiment
(An example of a sorting device which controls an oscillation element and an imaging element based on a state of fluid and fluid droplets)
2. Second Embodiment
(An example of a sorting device having a function of stabilizing pressure)

1. First Embodiment

Figure 1:
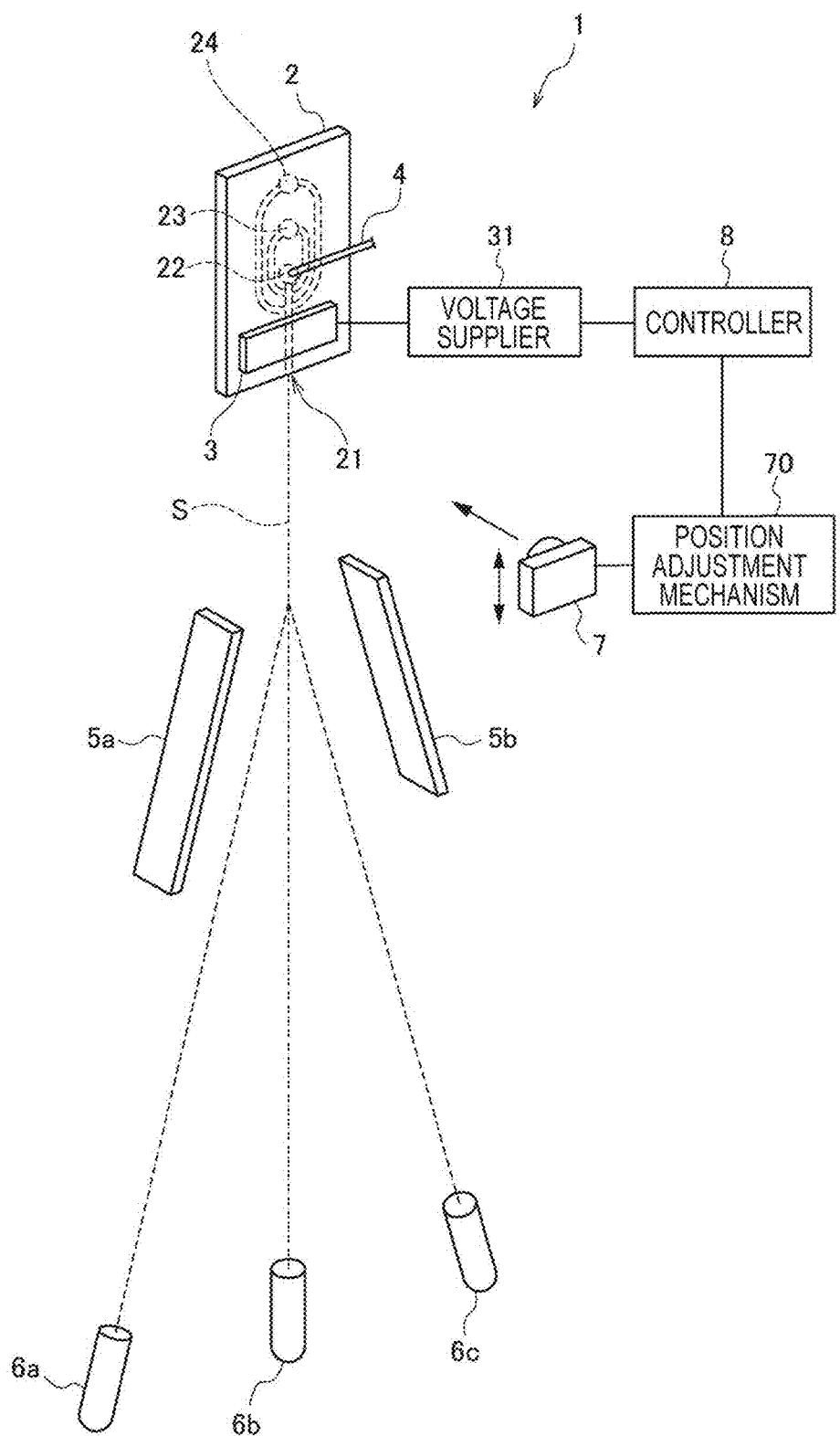
FIG. 1 is a schematic view showing a configuration of a microparticle sorting device according to a first embodiment of the present disclosure.

First, a microparticle sorting device according to a first embodiment of the present disclosure will be described. FIG. 1 is a view showing a schematic configuration of the microparticle sorting device according to the first embodiment of the present disclosure.
[Overall Configuration of Device]
A microparticle sorting device 1 of the present embodiment sorts and recovers microparticles based on results analyzed by an optical method. The microparticle sorting device 1 herein includes a microchip 2, an oscillation element 3, an electrode 4 for charging, deflection plates 5a and 5b, recovery containers 6a to 6c and the like, as shown in FIG. 1. Further, the microparticle sorting device 1 includes an imaging element (camera 7) and a controller 8. The camera 7 obtains an image of fluid and fluid droplets. The controller 8 controls driving voltage of the oscillation element 3 and/or a position of the camera 7 based on the image taken by the camera 7.

[Microparticle]

The microparticles analyzed and sorted by the microparticle sorting device 1 of the present embodiment broadly include cells, microorganisms, and biologically-relevant microparticles such as a ribosome, or include synthetic particles such as latex particles, gel particles and industrial particles.

Examples of the biologically-relevant microparticles include a chromosome, a ribosome, a mitochondrion, and an organelle, which are included in various cells. Further, examples of the cells include plant cells, animal cells, and blood cells. Moreover, examples of the microorganisms include bacteria such as an *E. coli*, viruses such as a tobacco mosaic virus, and fungi such as a yeast cell. These biologically-relevant microparticles may include biologically-relevant polymers such as nucleic acid, protein and a complex thereof.

On the other hand, examples of the industrial particles include particles including organic polymer materials, inorganic materials or metallic materials. As the organic polymer materials, for example, polystyrene, styrene divinyl benzene, and polymethyl methacrylate can be used. As the inorganic materials, for example, glass, silica, and magnetic materials can be used. As the metallic materials, for example, gold colloid and aluminum can be used. Note that these microparticles generally have a spherical shape, but may have a non-spherical shape. Further, the size and the mass thereof are not specifically restricted.

[Microchip 2]

The microchip 2 includes a sample inlet 22, a sheath inlet 23, a suction outlet 24 and the like. Liquid (sample liquid) including microparticles to be sorted is introduced to the sample inlet 22, while sheath liquid is introduced to the sheath inlet 23. The suction outlet 24 is for eliminating obstructions and bubbles. In this microchip 2, the sample liquid is introduced to the sample inlet 22 and joins the sheath liquid introduced to the sheath inlet 23. Then, the sample liquid is sent to a sample flow path and is discharged from an orifice 21 disposed at an end of the sample flow path.

To the sample flow path, a suction flow path which communicates with the suction outlet 24 is connected. When obstructions and bubbles appear in the sample flow path, this suction flow path applies negative pressure upon the inner side of the sample flow path to reverse the flow in the sample flow path temporarily in order to eliminate the obstructions and bubbles. A negative pressure source such as a vacuum pump is connected to the suction outlet 24.

The microchip 2 can be formed of glass or various plastics (such as PP, PC, COP, and PDMS). A preferable material for the microchip 2 is one which transmits measurement light emitted from a light detector, and has little autofluorescence as well as few optical errors due to small wavelength dispersion.

The microchip 2 can be formed by wet etching or dry etching of a glass substrate, or by nanoimprinting, mold injection, or a mechanical process of a plastic substrate. The microchip 2 can be formed, for example, by sealing a substrate, on which a sample flow path and the like are formed, with a substrate including a similar or a different material.

[Oscillation Element 3]

The oscillation element 3 is abutted on a part of the microchip 2 or disposed as an inner constituent of the microchip 2. The oscillation element 3 gives minute oscillation to the sheath liquid by oscillating the microchip 2 at a predetermined frequency. Then, the oscillation element 3 converts the fluid (sample liquid and sheath liquid) discharged from the orifice 21 into fluid droplets to generate a fluid stream (a fluid droplet stream) S. As the oscillation element 3, a piezo element and the like can be used.

[Voltage Supplier 31]

A voltage supplier 31 supplies driving voltage to the oscillation element 3. The driving voltage of the oscillation element 3 is supplied in accordance with a sine wave in order to form stable fluid droplets, and is controlled by both a frequency (clock value) and amplitude (drive value).

[Charged Section]

A charged section applies positive or negative charges to fluid droplets discharged from the orifice 21. The charged section herein includes, for example, the electrode 4 for charging and a voltage source which applies predetermined voltage to this electrode 4 for charging. The electrode 4 for charging is disposed while being brought into contact with the sheath liquid and/or the sample liquid, which flow through the flow path. The electrode 4 for charging herein further charges the sheath liquid and/or the sample liquid, and is inserted, for example, into a charged electrode inlet of the microchip 2.

In FIG. 1, the electrode 4 for charging is disposed so as to come into contact with the sample liquid. However, the present disclosure is not restricted thereto and the electrode 4 for charging may be disposed so as to come into contact with the sheath liquid or with both the sample liquid and the sheath liquid. However, it should be noted that the electrode 4 for charging is preferably disposed so as to come into contact with the sheath liquid, considering an influence on a cell to be sorted.

In this manner, by applying the positive or negative charges to desired fluid droplets and charging the fluid droplets, an arbitrary fluid droplet including microparticles can be isolated by electrical force. Further, when charging timing by the charged section is synchronized with supply of voltage to the oscillation element 3, only the arbitrary fluid droplet can be charged.

[Deflection Plates 5a, 5b]

The deflection plates 5a, 5b change a traveling direction of each fluid droplet within the fluid stream S by the electric force that acts between the deflection plates and the charges applied to the fluid droplets. The deflection plates 5a, 5b herein guide the traveling direction of each fluid droplet to a predetermined recovery container and are disposed while facing each other across the fluid stream S. As these deflection plates 5a, 5b, for example, electrodes which are generally used can be employed.

The positive voltage and the negative voltage are respectively applied to the deflection plates 5a and 5b. When charged fluid droplets pass through an electric field formed by the above-mentioned voltage application, electric force (coulomb force) occurs, and each fluid droplet is drawn in a direction of the deflection plate 5a or 5b. The microparticle sorting device 1 can control a direction of the fluid droplet stream (side stream) drawn to the electric field, by changing the polarity (positive or negative) or amount of charges applied to the fluid droplets. Therefore, a plurality of mutually different microparticles can be simultaneously sorted.

[Recovery Containers 6a to 6c]

The recovery containers 6a to 6c recover fluid droplets which have passed between the deflection plates 5a and 5b. As the recovery containers 6a to 6c for experiment, general-purpose plastic tubes or glass tubes can be used. It is preferable to switchably dispose these recovery containers 6a to 6c inside the device. Further, among these recovery containers 6a to 6c, one that receives microparticles which are not to be sorted may be coupled to a drainage path for the recovered fluid droplets.

Note that the number of the recovery containers disposed in the microparticle sorting device 1 is not specifically restricted. For example, in cases where more than three recovery containers are disposed, each fluid droplet may be guided to any one of those recovery containers and may be recovered depending on the presence or absence of electric acting force between the deflection plates 5a and 5b, and the magnitude of the force.

[Imaging Element (Camera) 7]

The imaging element (camera) 7 takes an image of the fluid before being converted into the fluid droplets and of the fluid droplets at a position (break-off point BP) where a laminar flow of the sample liquid and the sheath liquid discharged from the orifice 21 is converted into fluid droplets. Note that the image of the fluid and the fluid droplets can be taken by using various imaging elements such as a photoelectric conversion element other than the imaging device such as a CCD camera and a CMOS camera.

Further, the camera 7 preferably includes a position adjustment mechanism 70 in order to change the position of the camera 7. As a result, the position of the camera 7 can be easily controlled based on commands from the controller 8 (hereinafter described). The microparticle sorting device 1 according to the present embodiment may include not only the camera 7 but also a light source (not shown) which illuminates an imaging region.

[Controller 8]

The controller 8 controls driving electricity of the oscillation element 3 and/or the position of the camera 7 based on the image taken by the camera 7. More specifically, the controller 8 controls the voltage supplier 31 and the position adjustment mechanism 70 based on the state of the fluid, in the image, before being converted into the fluid droplets and/or based on a state of a satellite fluid droplet existing between the break-off point and the fluid droplet including microparticles.

The controller 8 may include, for example, an information processing device including a general-purpose processor, a main storage, a secondary storage and the like. In such a case, the voltage supplier 31 and the position adjustment mechanism 70 can be automatically controlled by inputting, to the controller 8, image data taken by the imaging element such as the camera 7, and by executing control algorithm which has been programmed. Such a computer program may be stored, for example, in a recording medium such as a magnetic disc, an optical disc, a magneto-optical disc, and a flash memory, or may be delivered through a network.

[Light Detector]

Further, the microparticle sorting device 1 according to the present embodiment includes, for example, the light detector (not shown) which irradiates a predetermined part of the sample flow path with light (measurement light) and detects light (light to be measured) emitted from microparticles which pass through the sample flow path. The light detector herein can be configured similarly to a flow cytometry in the related art. More specifically, the light detector herein includes a laser light source, an irradiating system, and a detecting system. The irradiating system includes, for example, a condenser lens which condenses a laser beam and irradiates microparticles with the laser beam, a dichroic mirror, and a band-pass filter. The detecting system detects the light to be measured which is emitted from the microparticles due to the laser beam irradiation.

The detecting system includes, for example, a photo multiplier tube (PMT) and an area imaging element such as a CCD, and a CMOS element. Note that the irradiating system and the detecting system may include the same single optical path or may separately include an individual optical path. Further, the light to be measured which is detected by the detecting system of the light detector is light emitted from the microparticles due to irradiation of the measurement light. For example, the light to be measured may be scattered light such as forward-scattered light, side-scattered light, Rayleigh scattered light and Mie scattered light, or fluorescence. The light to be measured is converted into electric signals. Optical characteristics of the microparticles are detected based on the electric signals.

[Movement]

Next, a movement of the microparticle sorting device 1 according to the present embodiment will be described. When microparticles are sorted by the microparticle sorting device 1 according to the present embodiment, the sample liquid including the microparticles to be sorted is introduced to the sample inlet 22, while the sheath liquid is introduced to the sheath inlet 23. Further, the optical characteristics of the microparticles as well as velocity (flow speed) of the microparticles and intervals of the microparticles are detected at the same time, for example, by using the light detector. The detected optical characteristics, flow speed, intervals of the microparticles and the like are converted into electric signals and are output to the whole controller (not shown) of the device.

The laminar flow of the sample liquid and the sheath liquid passes through a part to be irradiated with light in the sample flow path. Then, the laminar flow is discharged from the orifice 21 to a space outside the microchip 2. On this occasion, the orifice 21 is oscillated by the oscillation element 3, and fluid to be discharged is converted into fluid droplets. The traveling direction of each fluid droplet charged in the sample flow path is changed by the deflection plates 5a, 5b based on the detected results from the light detector. Then, each fluid droplet is guided to the predetermined recovery containers 6a to 6c and recovered.

In the series of processes, the microparticle sorting device 1 according to the present embodiment obtains the image of the fluid and the fluid droplets at the break-off point by using the camera 7. Then, the microparticle sorting device 1 controls the oscillation element 3 and the camera 7 by using the controller 8 based on the image. More specifically, the controller 8 controls the driving voltage supplied from the voltage supplier 31 and/or the position of the camera 7 based on the state of the fluid in the image and/or the state of the satellite fluid droplet.

(Imaging Process)

Figure 2:
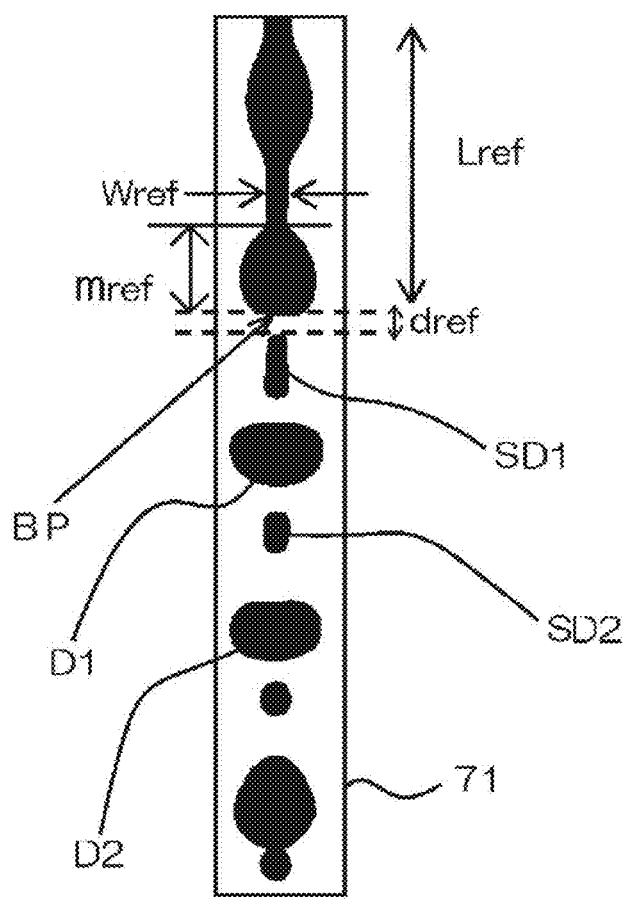
FIG. 2 is a schematic view showing an exemplary image taken by a camera 7 shown in FIG. 1.

FIG. 2 is a schematic view showing an exemplary image taken by the camera 7. As shown in FIG. 2, an image 71 obtained by the camera 7 includes at least a break-off point BP and a first satellite $SD_1$. Herein, the "break-off point BP" is a position where the fluid discharged from the orifice 21 is converted into fluid droplets. Further, the "first satellite $SD_1$" herein is a satellite fluid droplet SD which does not include microparticles and exists between the break-off point BP and a fluid droplet $D_1$, among fluid droplets D including the microparticles, which is closest to the break-off point BP.

(Controlling Driving Voltage)

Figure 3:
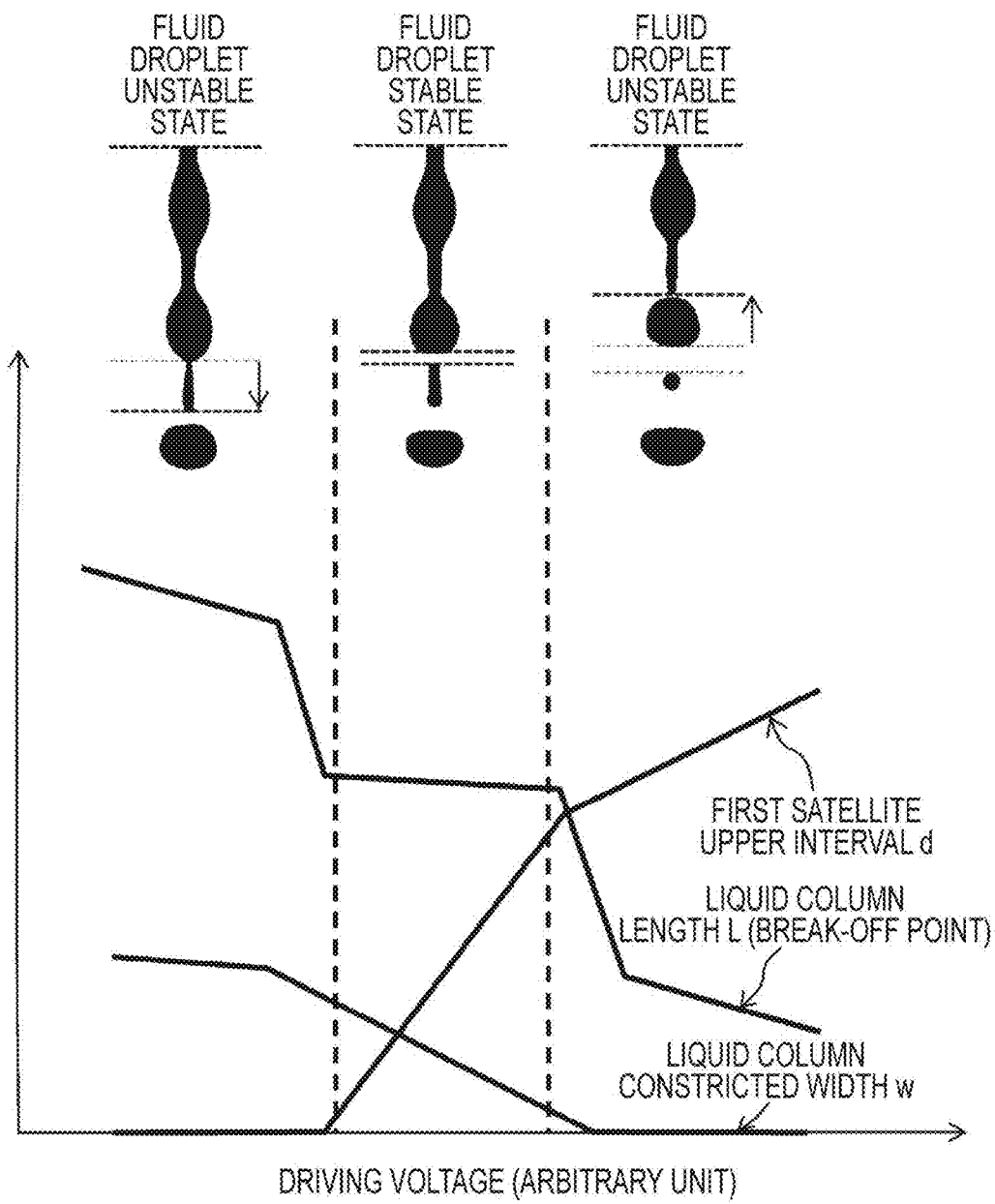
FIG. 3 is a view showing a relation between states of fluid and fluid droplets, and each parameter.

In cases where the driving voltage of the oscillation element 3 is controlled by the controller 8, for example, an image (reference image) in which the fluid and the fluid droplets are adjusted to be in the most preferable state is prepared in advance. Then, the driving voltage is adjusted so that an image during sorting matches with the reference image. The reference image and the image during sorting can be compared, for example, based on a distance d from the break-off point BP to the first satellite $SD_1$ (first satellite upper interval d), and based on a width w of the constricted region (liquid column constricted width) of the fluid right before being converted into fluid droplets. FIG. 3 is a view showing a relation between the states of the fluid stream S and each parameter.

When the first satellite upper interval d is narrower than when a fluid droplet is stable, such a state represents that the break-off point BP and the first satellite $SD_1$ are getting closer. In cases where a value of the first satellite upper interval d becomes smaller, or zero, such a state represents that a position of the break-off point BP has dropped by the first satellite $SD_1$ (fluid droplet unstable state shown in FIG. 3).

In cases where the liquid column constricted width w is narrow, such a state represents that the liquid column is about to be cut off. In cases where a value of the liquid column constricted width w becomes smaller, or zero, the liquid column is completely cut off and a new fluid droplet D is formed. Such a state represents that the break-off point BP has risen by the newly formed fluid droplet D (fluid droplet unstable state shown in FIG. 3).

The first satellite upper interval d, the liquid column constricted width w, and a liquid column length L (the position of the break-off point BP) have a mutually close relation. The liquid column length L, the first satellite upper interval d, and the liquid column constricted width w are indexes which directly show stability of the break-off point BP. Based on the value of the first satellite upper interval d or the value of the liquid column constricted width w, a fluid droplet shape of the fluid stream S can be stabilized by controlling the driving voltage of the oscillation element 3.

Figure 4A:
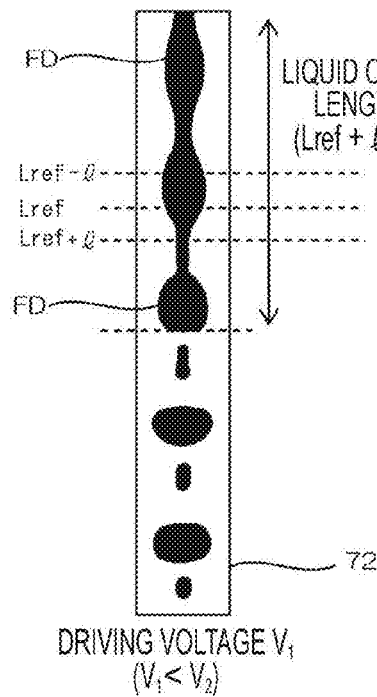
FIGS. 4A and 4B are views showing a relation between driving voltage of an oscillation element 3 and a liquid column length.
Figure 4B:
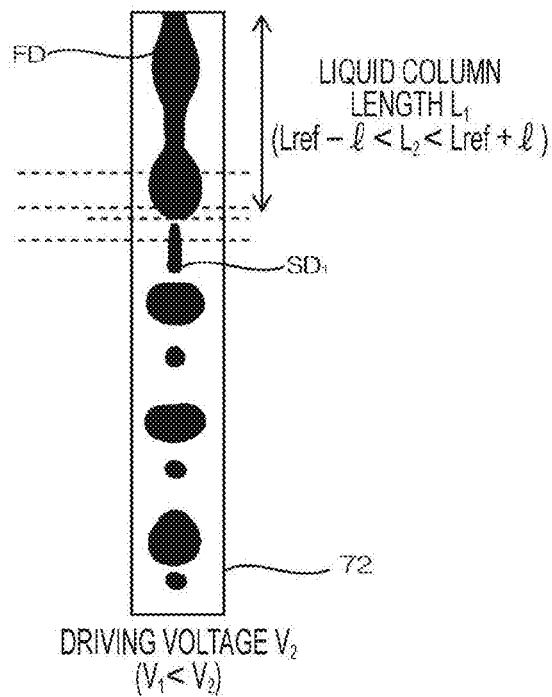
Figure 5A:
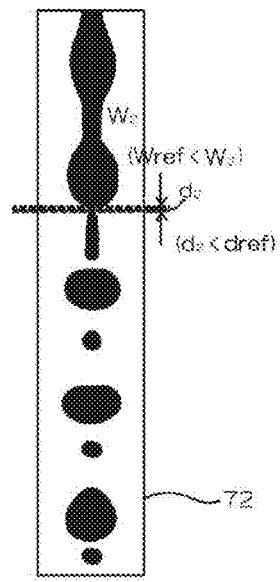
FIGS. 5A to 5C are views showing a relation between the driving voltage of the oscillation element 3, and a first satellite upper interval d and a liquid column constricted width w.
Figure 5B:
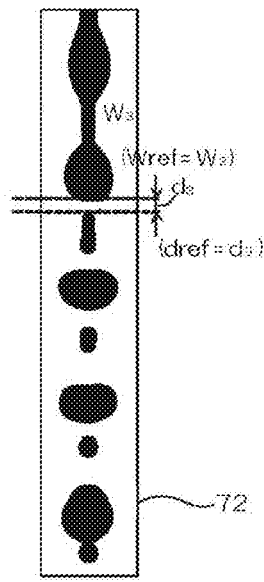
Figure 5C:
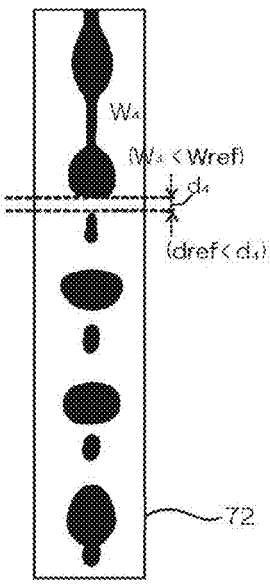

FIGS. 4A and 4B are views showing a relation between the driving voltage of the oscillation element 3 and the liquid column length L. FIGS. 5A to 5C are views showing a relation between the driving voltage of the oscillation element 3, and the first satellite upper interval d and the liquid column constricted width w. For example, in cases where the image 71 shown in FIG. 2 is regarded as a reference image, the driving voltage of the oscillation element 3 is controlled by the controller 8 so that the liquid column length L in an image 72 during sorting becomes $L_{ref} \pm l$ (l represents an arbitrary number of a pixel). As a result, the number of fluid droplets FD, inside the liquid column, which are included in the fluid right before being converted into fluid droplets becomes constant. The "fluid droplet inside the liquid column" herein represents a fluid droplet, before being separated, which is included in the fluid before being converted into fluid droplets.

As shown in FIGS. 4A and 4B, in cases where the driving voltage of the oscillation element 3 increases, the liquid column is cut off, and the fluid droplet FD, inside the liquid column, which is closest to the break-off point BP is converted into fluid droplets. As a result, the position of the break-off point BP rises, and the value of the liquid column length L decreases. By contrast, in cases where the driving voltage of the oscillation element 3 decreases, the first satellite $SD_1$ becomes large and is converted into a liquid column, and into a fluid droplet FD inside the liquid column. As a result, the position of the break-off point BP drops, and the value of the liquid column length L increases.

The controller 8 utilizes this relation to control the driving voltage of the oscillation element 3. Note that, under a state where sheath flow speed is constant, no change occurs in fluid droplet intervals. Further, a change in the position of the break-off point BP, which is caused by the change in the fluid droplet intervals, does not occur, either. Therefore, the driving voltage of the oscillation element 3 can be controlled so as to meet desired conditions easily.

Next, the driving voltage of the oscillation element 3 is controlled so that the first satellite upper interval d in the image 72 during sorting becomes similar to a first satellite upper interval $d_{ref}$ in the reference image 71 shown in FIG. 2. As shown in FIGS. 5A to 5C, in cases where the driving voltage of the oscillation element 3 increases, the value of the first satellite upper interval d increases. By contrast, in cases where the driving voltage of the oscillation element 3 decreases, the value of the first satellite upper interval d decreases. The controller 8 utilizes this relation to control the driving voltage of the oscillation element 3.

The first satellite upper interval d is sensitive to a change in the fluid droplet shape of the fluid stream S. Therefore, the fluid droplet shape during sorting can be maintained as stable as a state similar to the reference image by keeping adjusting the first satellite upper interval d so as to match with the first satellite upper interval $d_{ref}$ of the reference image 71.

Further, instead of the above-mentioned first satellite upper interval $d_{ref}$, the driving voltage of the oscillation element 3 can be controlled by using the liquid column constricted width w. More specifically, the driving voltage of the oscillation element 3 is controlled so that the value of the liquid column constricted width w in the image 72 during sorting becomes similar to a liquid column constricted width $w_{ref}$ of the reference image 71 shown in FIG. 2. As shown in FIGS. 5A to 5C, in cases where the driving voltage of the oscillation element 3 increases, a value of the liquid column constricted width w decreases. In cases where the driving voltage of the oscillation element 3 decreases, a value of the liquid column constricted width w increases. The controller 8 utilizes this relation to control the driving voltage of the oscillation element 3.

Similar to the above-mentioned first satellite upper interval $d_{ref}$, the liquid column constricted width w sensitively changes with respect to the change in fluid droplet shape of the fluid stream S. Therefore, the fluid stream S can be maintained in a stable state, and also the position of the break-off point BP can be stabilized by keeping adjusting the liquid column constricted width w so as to match with the liquid column constricted width $w_{ref}$ of the reference image 71.

Note that, in controlling the driving voltage of the oscillation element 3 by the controller 8, either the first satellite upper interval d or the liquid column constricted width w may be an index. However, the fluid droplet shape of the fluid stream S can be further stabilized by using both of them as indexes.

Figure 6:
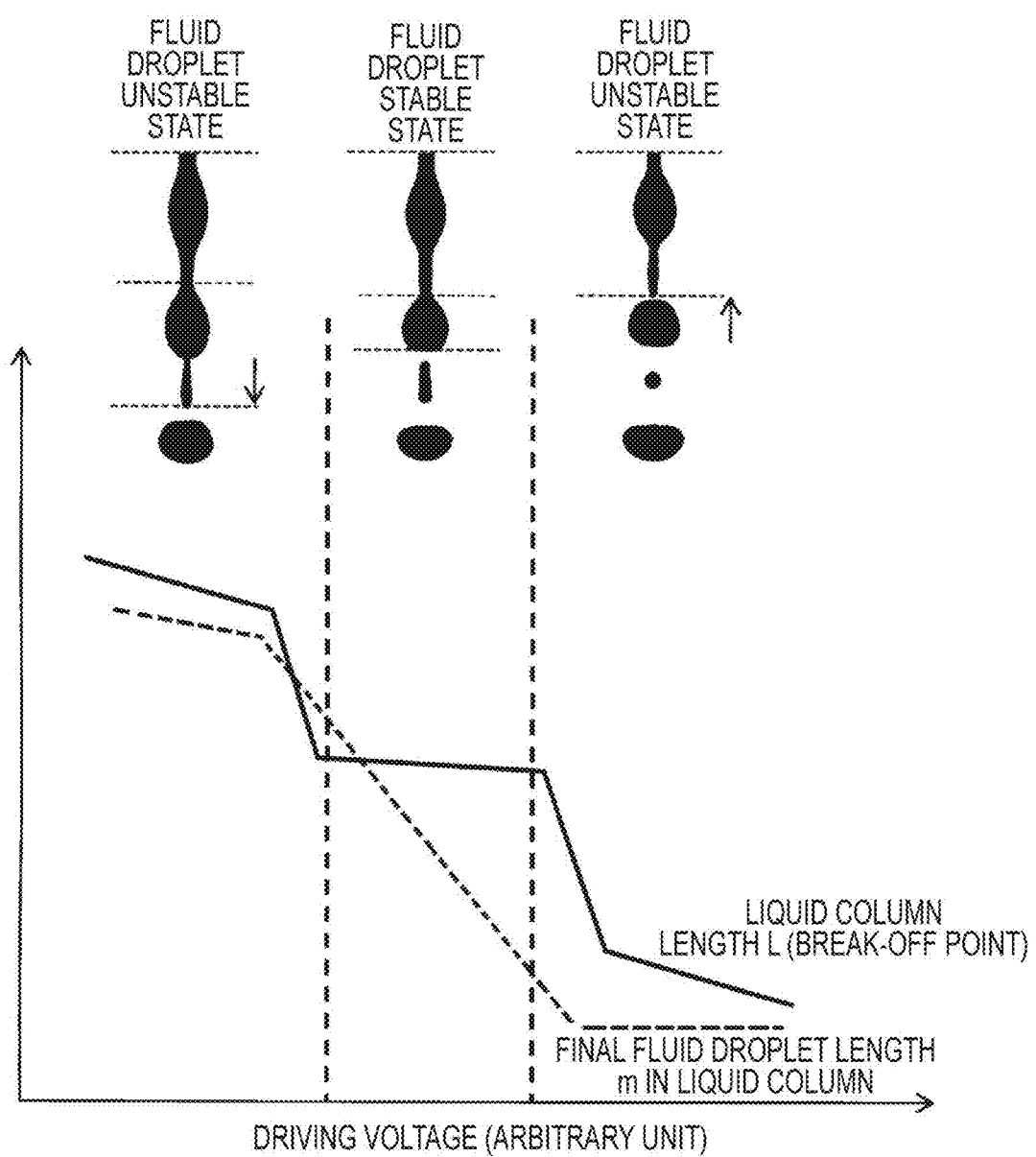
FIG. 6 is a view showing a relation between states of fluid and each parameter.
Figures 7A, 7B, 7C:
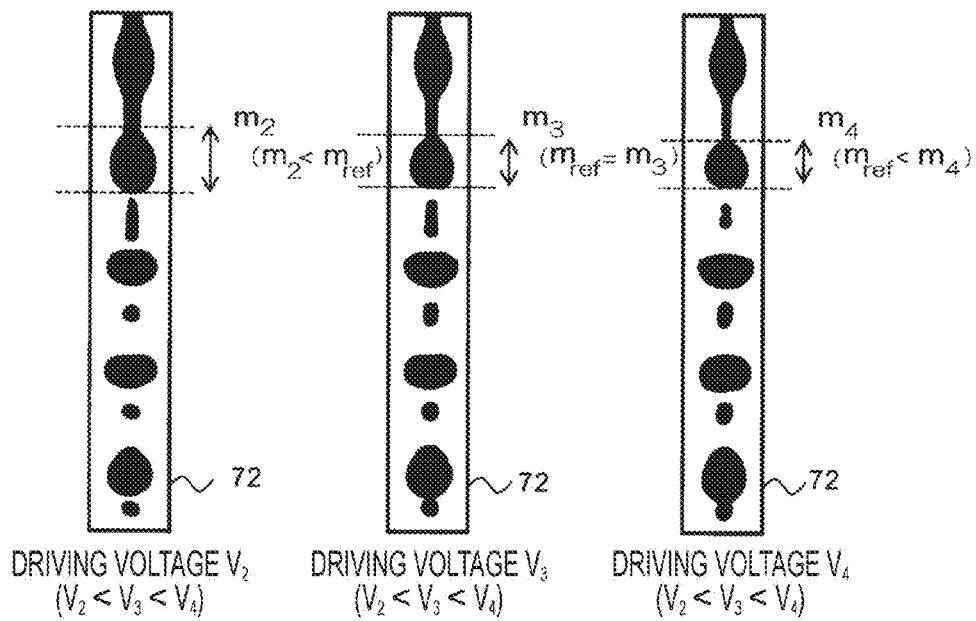
FIGS. 7A to 7C are views showing a relation between the driving voltage of the oscillation element 3 and a final fluid droplet length m in a liquid column.

Alternatively, the driving voltage of the oscillation element 3 can be controlled based only on the state of the fluid without using the state of the satellite fluid droplet. FIG. 6 is a view showing a relation between the states of fluid, and the liquid column length L and a final fluid droplet length m in the liquid column. FIGS. 7A to 7C are views showing a relation between the driving voltage of the oscillation element 3 and the final fluid droplet length m in the liquid column.

As shown in FIG. 6, a distance m (final fluid droplet length in the liquid column) from a position where the liquid column constricted width w becomes minimum (narrowest part of the constricted region), to the break-off point has a close relation with the liquid column length L (the position of the break-off point BP). Therefore, the final fluid droplet length m in the liquid column is an index which directly shows the stability of the break-off point BP. Based on a value of the final fluid droplet length m in the liquid column, the fluid droplet shape of the fluid stream S can be stabilized by controlling the driving voltage of the oscillation element 3.

More specifically, the driving voltage of the oscillation element 3 is controlled so that the value of the final fluid droplet length m in the liquid column in the image 72 during sorting becomes similar to a final fluid droplet length $m_{ref}$ in the liquid column of the reference image 71 shown in FIG. 2. As shown in FIGS. 7A to 7C, in cases where the driving voltage of the oscillation element 3 increases, the value of the final fluid droplet length m in the liquid column decreases. On the other hands, in cases where the driving voltage of the oscillation element 3 decreases, the value of the final fluid droplet length m in the liquid column increases. The controller 8 utilizes this relation to control the driving voltage of the oscillation element 3.

In this manner, even in a case where no satellite fluid droplet is formed or a radius of an orifice is large, the fluid droplet shape of the fluid stream S can be stabilized by controlling the driving voltage of the oscillation element 3 with an index of the final fluid droplet length m in the liquid column. Further, the final fluid droplet length m in the liquid column is sensitive to the change in the fluid droplet shape of the fluid stream S. Therefore, fluid droplet formation during sorting can be maintained as stable as the state similar to the reference image by keeping adjusting the final fluid droplet length m in the liquid column so as to match the final fluid droplet length $m_{ref}$ in the liquid column of the reference image 71.

Note that, for example, in cases where a plurality of the narrowest parts (positions where the liquid column constricted width w becomes minimum) exists in the constricted region of the fluid right before being converted into fluid droplets, an arbitrary point, for example, a central point of the constricted region or a point closest to the break-off point BP may be regarded as the narrowest part. Then, the final fluid droplet length m in the liquid column may be determined. Further, the final fluid droplet length m in the liquid column may independently be an index for controlling the driving voltage of the oscillation element 3. However, the driving voltage of the oscillation element 3 can be controlled based on both the above-mentioned first satellite upper interval d and the liquid column constricted width w.

Figures 8A, 8B:
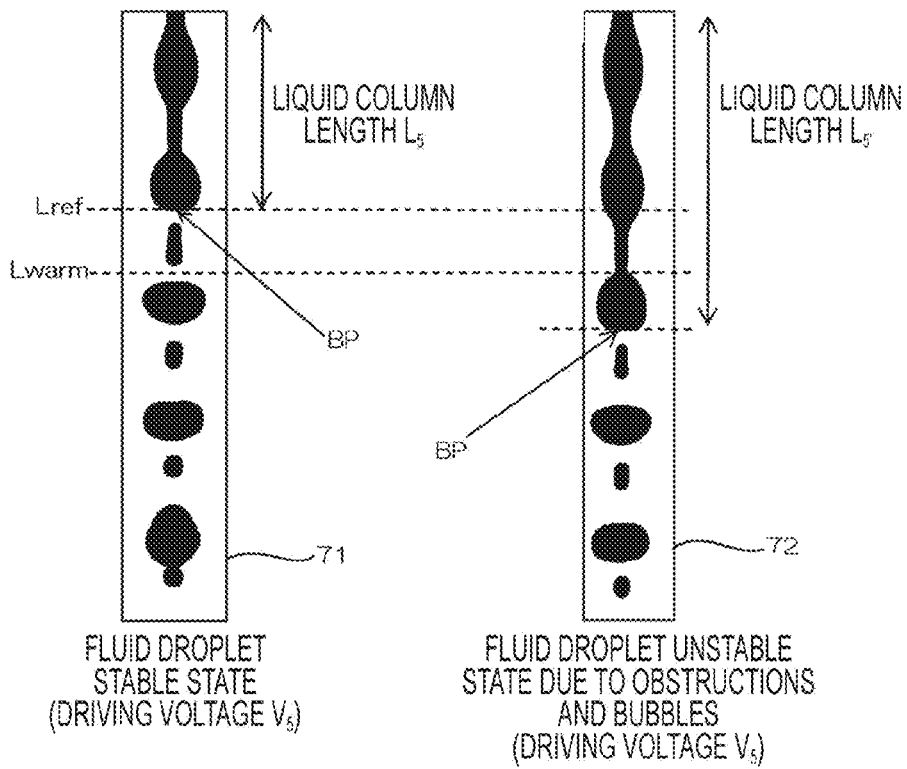
FIGS. 8A and 8B are schematic views showing an anomaly detecting method based on a liquid column length L.

On the other hand, during sorting, there is a case where the fluid droplet formation cannot be maintained stable and the break-off point BP drastically drops because of the obstructions in the flow path and interfusion of bubbles. However, such a situation can be detected based on the liquid column length L. FIGS. 8A and 8B are schematic views showing an anomaly detecting method based on the liquid column length L. In cases where an anomaly such as the obstructions in the flow path and interfusion of bubbles occurs, the liquid column length L drastically increases. Therefore, for example, a liquid column length $L_{warn}$ for detecting an anomaly is set in addition to a liquid column length $L_{ref}$ as shown in FIG. 8A. When the liquid column length L exceeds this value as shown in FIG. 8B, it is determined that "an anomaly has occurred".

When the fluid droplet formation of the fluid stream S becomes unstable, sorting performance cannot be maintained. Therefore, in cases where an anomaly is detected, charging of the fluid droplets and application of voltage to the deflection plates are halted. Further, in such a case, sorting is stopped, and notification is given to a user. At the same time, suction is carried out from the suction outlet 24 disposed in the microchip 2. As a result, stability of the flow path (laminar flow) can be achieved. In cases where the liquid column length L falls again below the liquid column length $L_{warn}$ for detecting an anomaly, the above-mentioned control process is carried out assuming that the flow path (laminar flow) has been stabilized.

(Controlling Camera Position)

FIGS. 9A and 9B are views showing a changing status of the fluid stream due to a change in environmental temperature. As shown in FIGS. 9A and 9B, when a sheath liquid temperature changes due to the change in the environmental temperature during sorting, the fluid droplet intervals of the fluid stream S change because the flow speed changes due to a change in viscosity. Further, the position of the break-off point BP, that is, the liquid column length L changes as well. As a result, the number of the fluid droplets FD inside the liquid column in the image 72 changes. At the same time, there is a possibility that the break-off point BP cannot be stably detected or discriminated.

Under a condition in which the fluid droplet shape and pressure of the fluid stream S are stable, it can be considered that an influence on the liquid column length L is caused by the change in the fluid droplet intervals which is caused by the change in temperature. Accordingly, in the microparticle sorting device 1 according to the embodiment, the position of the camera 7 is moved with the controller 8 depending on the change in the liquid column length L in the image. As a result, the position of the break-off point BP in the image and the number of fluid droplets FD inside the liquid column can be maintained at a constant level. Therefore, a drop delay time can be maintained at a constant value as well.

FIGS. 10A and 10B are views showing a method for moving the position of the camera 7 as the position of the break-off point changes. For example, in the method, the liquid column length $L_{ref}$ can be obtained from the reference image shown in FIG. 2. Further, as shown in FIGS. 10A and 10B, when the liquid column length L in the image 72 during sorting exceeds a range of $L_{ref} \pm m$ (m represents an arbitrary number of a pixel), a position P of the camera 7 is controlled by the controller 8 so as to negate the change in the liquid column length L.

In cases where the fluid droplet intervals broaden and the break-off point BP drops because of an increase in the flow speed due to an increase in temperature, the value of the liquid column length L increases. Accordingly, the position of the camera 7 is lowered (P→P'). Further, in cases where the fluid droplet intervals have narrowed, the position of the camera 7 rises (P'→P) in accordance with a decrease in the liquid column length L.

In such a manner, when the position of the camera 7 is made to follow the change in the position of the break-off point BP, the value of the liquid column length L in the image can be maintained constant. As a result, in a sorting image, the break-off point BP is stably maintained at a predetermined position corresponding to the reference image. Therefore, the number of the fluid droplets FD inside the liquid column can be maintained constant, and the drop delay time adjusted in advance can be maintained for a long time.

Figure 11:
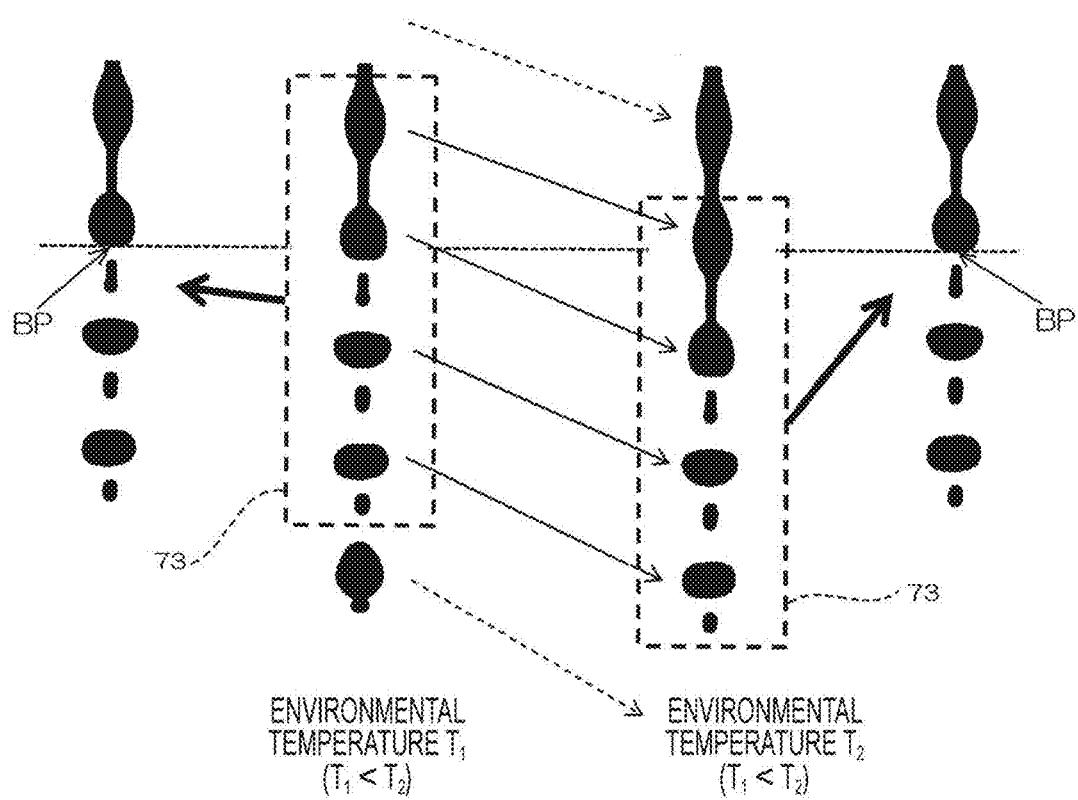
FIG. 11 is a view showing other methods for maintaining a constant position of the break-off point.

As a method for constantly maintaining the position of the break-off point BP in the image other than a method for moving the camera 7 itself, there is a method for changing an image cutting position. FIG. 11 is a view showing other methods for making the position of the break-off point constant. For example, an image of fluid and fluid droplets are taken with a wide-angle camera as shown in FIG. 11. From the image, an image 73 including a break-off point BP is cut out so as to be used for control by the controller 8.

In such a case, when a position of the break-off point BP changes, the image cutting position is also changed so as to control the change in the value of the liquid column length L. As a result, it is possible to simulate control of an imaging position as the break-off point BP moves.

The microparticle sorting device according to the present embodiment controls the driving voltage of the oscillation element and/or the position of the imaging element based on the state of the fluid stream S. Therefore, it is possible to stabilize the fluid droplet shape for a prolonged period of time and to maintain the break-off point BP with high accuracy. The microparticle sorting device according to the present embodiment performs control by using a parameter which sensitively reacts to the change in the fluid droplet shape. Therefore, the fluid droplet shape can be controlled with high stability, fast-response, and robustness.

Further, in the microparticle sorting device according to the present embodiment, stability of the flow path can be achieved by immediate detection of the obstructions in the flow path and interfusion of bubbles during sorting and emergency stop of sorting as well as automatic suction inside the flow path. Further, in the microparticle sorting device according to the present embodiment, the position of the camera 7 can follow the change in the sheath flow speed caused by the change in the environmental temperature, and the change in the break-off point BP due to the change in the sheath flow speed. Accordingly, the number of the fluid droplets FD inside the liquid column to the break-off point BP can be maintained constant, and the drop delay time adjusted in advance can be maintained for a long time, and also the sorting performance can be maintained.

As a result, according to the microparticle sorting device of the present embodiment, influences due to the change in the environmental temperature, a decrease of the sheath liquid/sample liquid, the obstructions and interfusion of bubbles, or the change in the fluid droplet shape can be controlled. Therefore, it is possible to achieve stable sorting with high accuracy over a prolonged period of time.

In the above-mentioned first embodiment, the example using the microchip 2 has been described. However, the present disclosure is not restricted thereto. Even in a case where a flow cell is used instead of the microchip 2, a similar effect can be obtained. Further, the light detector of the present disclosure may be replaced with an electric or magnetic detecting unit.

2. Second Embodiment

Figure 12:
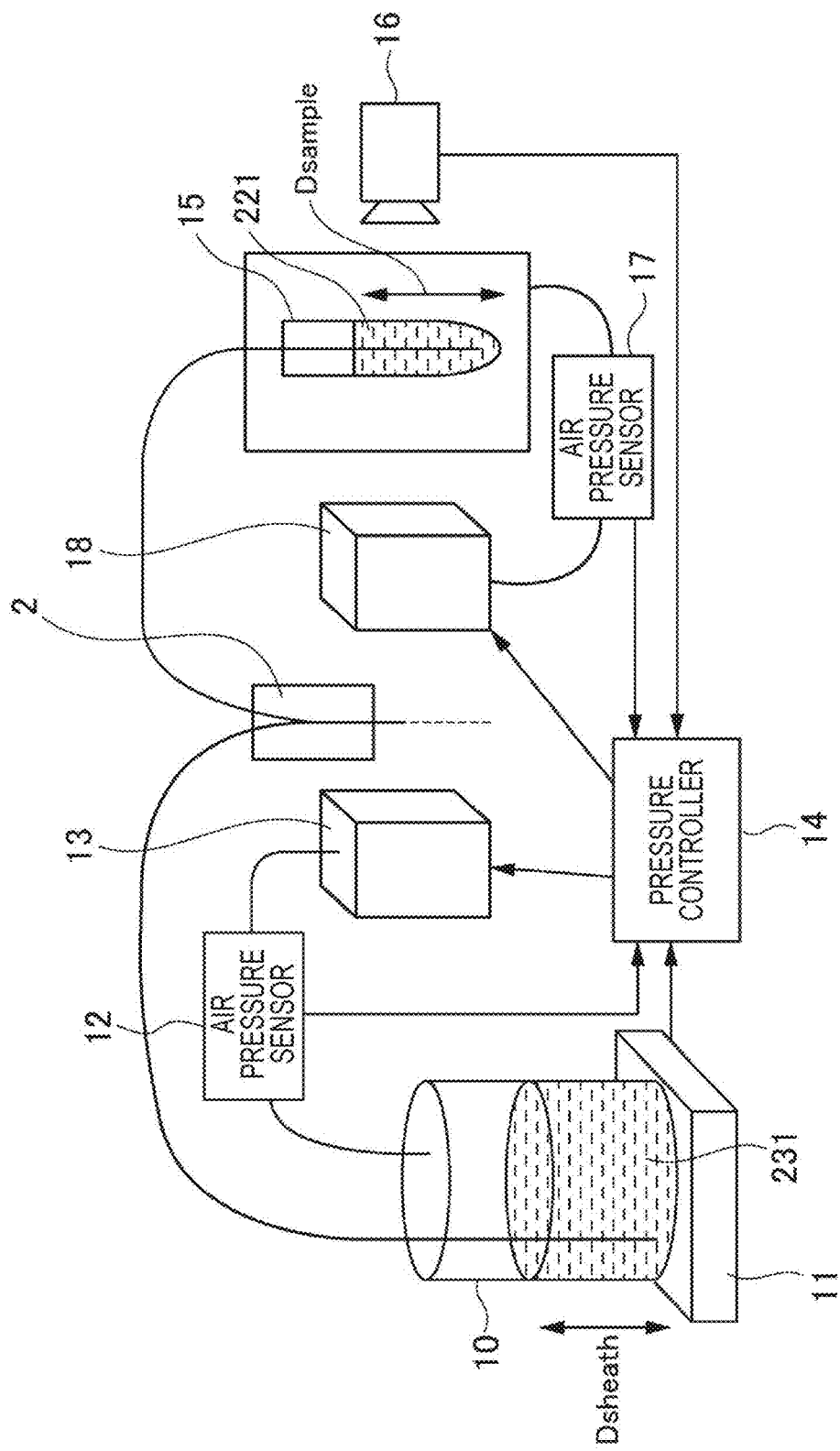
FIG. 12 is a schematic view showing an overall configuration of a microparticle sorting device according to a second embodiment of the present disclosure.

Next, a microparticle sorting device according to a second embodiment of the present disclosure will be described. FIG. 12 is a schematic view of an overall configuration of the microparticle sorting device according to the second embodiment of the present disclosure. As shown in FIG. 12, the microparticle sorting device according to the present embodiment further includes a function of stabilizing pressure in addition to the configuration of the above-mentioned first embodiment.

Figure 13A:
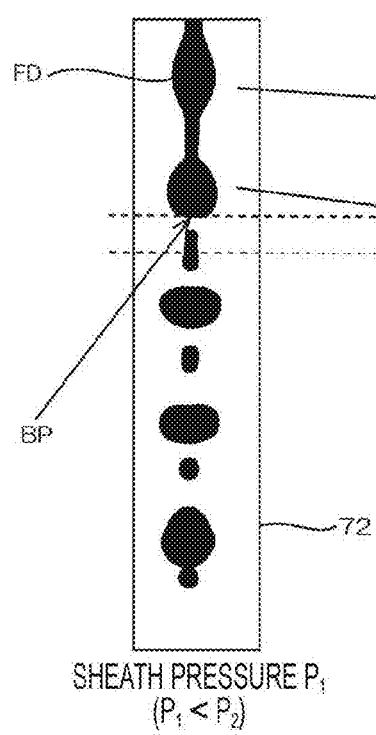
FIGS. 13A and 13B are views showing a relation between sheath pressure, and a state of fluid and fluid droplets.
Figure 13B:
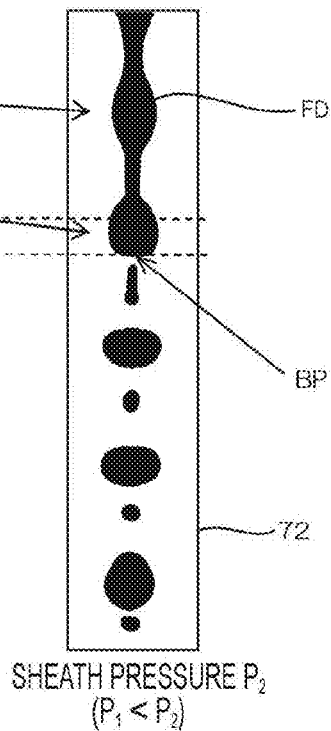

The fluid droplet formation state of the fluid stream S discharged from the orifice 21 changes depending on the sheath pressure. FIGS. 13A and 13B are views showing a relation between the sheath pressure and the state of the fluid and the fluid droplets. As shown in FIGS. 13A and 13B, when the sheath pressure is low, a position of the break-off point BP rises. On the other hand, when the sheath pressure is high, the position of the break-off point BP drops because the flow speed increases.

Regarding sample flow, when sample pressure is low, an event rate (the number of detection per unit time) decreases. On the other hand, when the sample pressure is high, the event rate increases. In addition to air pressure controlled by compressors 13 and 18, pressure obtained by adding fluid pressure depending on a water depth is applied to an intake disposed at the bottom of a sheath container 10 or a sample container 15. In the microparticle sorting device according to the present embodiment, to stabilize the pressure, a setting value of the air pressure is controlled depending on a change in the fluid pressure due to a decrease in the water depth that occurs after sorting.

Figure 14:
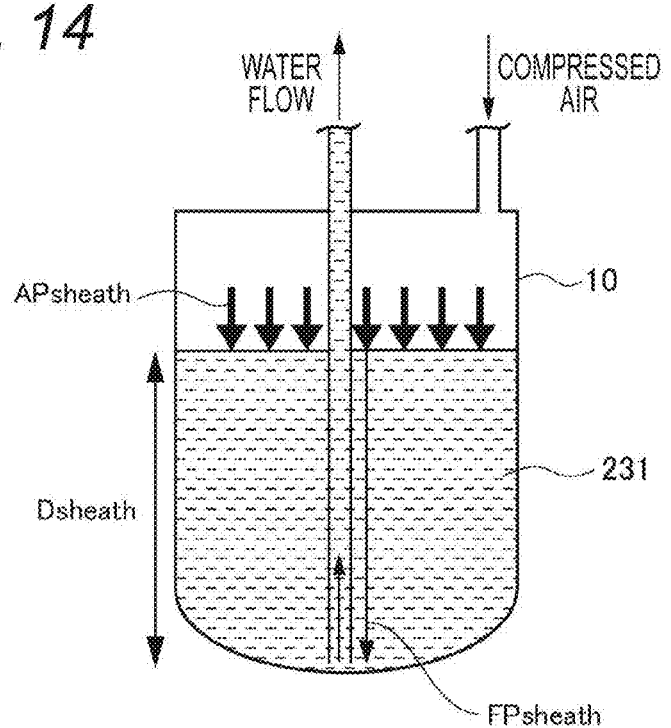
FIG. 14 is a schematic view showing air pressure and water pressure inside a sheath container 10.
Figure 15:
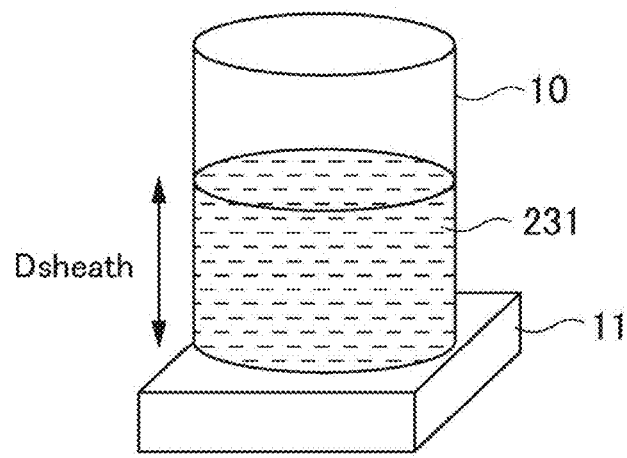
FIG. 15 is a view showing a method for measuring a water depth $D_{sheath}$ of sheath liquid 231.
Figure 16:
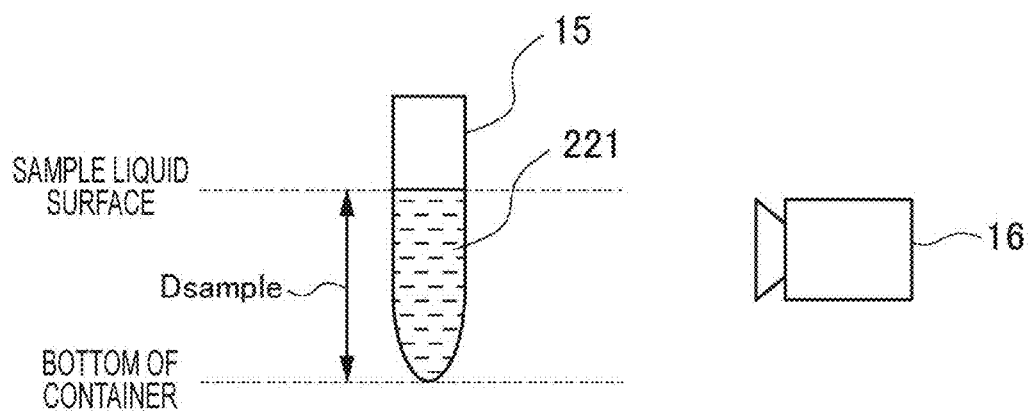
FIG. 16 is a view showing a method for measuring a water depth $D_{sample}$ of sample liquid 221.
Figure 17A:
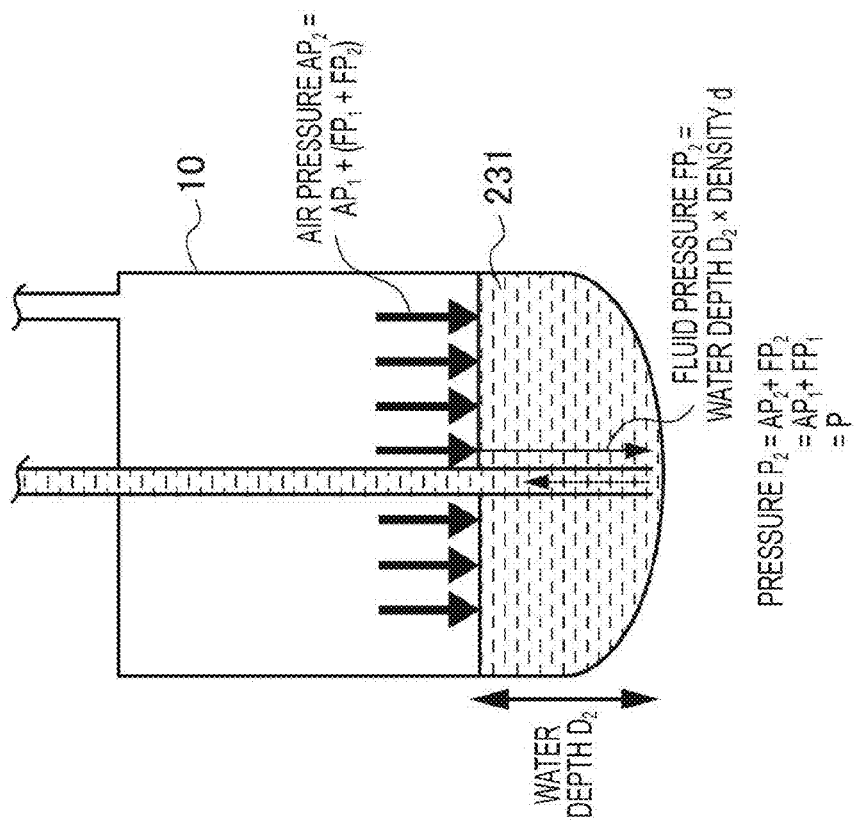
FIGS. 17A and 17B are views showing a method for controlling the sheath pressure.
Figure 17B:
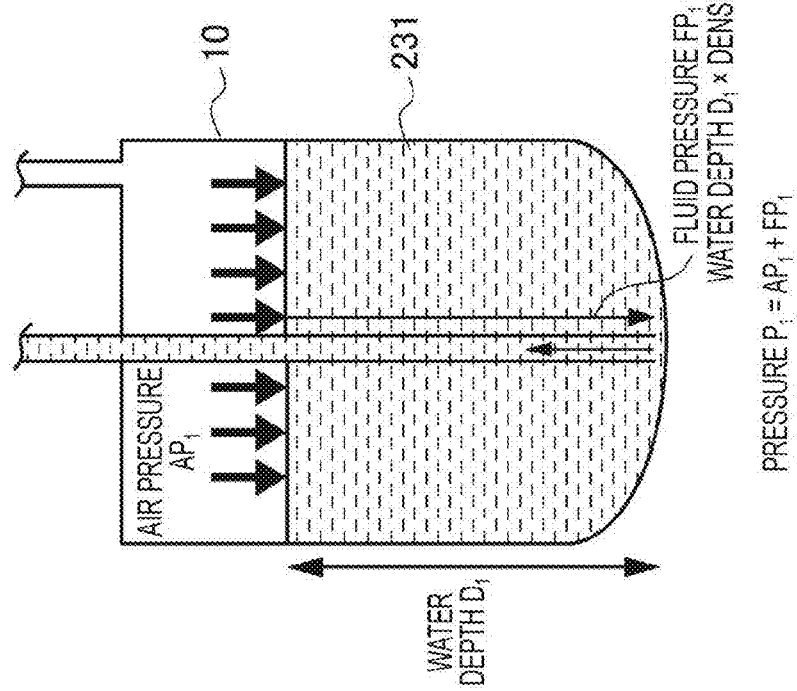

FIG. 14 is a schematic view showing the air pressure and water pressure inside the sheath container 10. FIG. 15 is a view showing a method for measuring a water depth $D_{sheath}$ of sheath liquid 231. FIG. 16 is a view showing a method for measuring a water depth $D_{sample}$ of sample liquid 221. FIGS. 17A and 17B are views showing a method for controlling the sheath pressure. In the microparticle sorting device according to the present embodiment, the water depth $D_{sheath}$ of the sheath liquid 231 and/or the water depth $D_{sample}$ of the sample liquid 221 are measured.

As shown in FIGS. 14 and 15, the water depth $D_{sheath}$ of the sheath liquid 231 can be calculated from the known mass and cross-sectional area of the sheath container 10 and from the density of the sheath liquid 231 by measuring the whole mass including the sheath container 10 with a scale 11. On the other hand, as shown in FIG. 16, the water depth $D_{sample}$ of the sample liquid 221 can be calculated by detecting a bottom of the sample container 15 and a liquid surface of the sample liquid 221 based on the image obtained by a camera 16, and by converting a pixel distance between two points in the image to an actual distance.

Then, fluid pressure $FP_{sheath}$ of the sheath liquid 231 and fluid pressure $FP_{sample}$ of the sample liquid 221 are respectively calculated based on the water depth $D_{sheath}$ of the sheath liquid 231 and the water depth $D_{sample}$ of the sample liquid 221. In such a case, the density of the sheath liquid 231 can be easily calculated based on the known density. Further, the density of the sample liquid 221 is almost similar to that of the sheath liquid 231 and can be calculated from the density of the sheath liquid 231.

As shown in FIGS. 17A and 17B, a pressure controller 14 sets air pressure $AP_{sheath}$ and gives an instruction to the compressor 13 to negate a change in the fluid pressure $FP_{sheath}$ due to a decrease in the water depth $D_{sheath}$, so that the sheath pressure $P_{sheath}$ becomes constant. Herein, the sheath pressure $P_{sheath}$ is equal to a sum of the air pressure $AP_{sheath}$ and the fluid pressure $FP_{sheath}$ ($P_{sheath}=AP_{sheath}+FP_{sheath}$). Therefore, the sheath pressure $P_{sheath}$ can be stabilized for a prolonged period of time without any change by periodically calculating the fluid pressure $FP_{sheath}$ and setting the air pressure $AP_{sheath}$ in accordance with the calculated fluid pressure $FP_{sheath}$.

Further, the pressure controller 14 can control the sample pressure $P_{sample}$ instead of controlling the above-mentioned sheath pressure $P_{sheath}$, or together with controlling the sheath pressure $P_{sheath}$. Even in such a case, similar to the above-mentioned sheath pressure $P_{sheath}$, the pressure controller sets the air pressure $AP_{sample}$ depending on the fluid pressure $FP_{sample}$ and gives an instruction to the compressor 18. As a result, the sample pressure $P_{sample}$ can be stabilized for a prolonged period of time.

In the microparticle sorting device according to the present embodiment, the air pressure is adjusted so that a sum of the air pressure and the fluid pressure in the sheath liquid becomes constant. Therefore, the change in the fluid pressure due to the decrease in the water depth of the sheath liquid is controlled, and it is possible to achieve constant and stable sheath flow for a prolonged period of time. Further, in the microparticle sorting device according to the present embodiment, the change in the air pressure and in the fluid pressure of the sample liquid is controlled together with controlling the sheath pressure, or instead of controlling the sheath pressure. Therefore, it is possible to achieve sorting which maintains a constant event rate for a prolonged period of time.

Note that configurations and effects other than those described hereinbefore of the microparticle sorting device according to the present embodiment are similar to those described in the above-mentioned first embodiment.

Further, the present disclosure may have configurations hereinafter described.

(1)

A microparticle sorting device including:

an imaging element configured to obtain an image of fluid and fluid droplets at a position where the fluid discharged from an orifice which generates a fluid stream is converted into the fluid droplets; and a controller configured to control driving voltage of an oscillation element which gives oscillation to the orifice and/or control a position of the imaging element, based on a state of the fluid in the image and/or a state of a satellite fluid droplet which does not include microparticles and exists between the position, where the fluid is converted into the fluid droplets, and a fluid droplet, among fluid droplets including the microparticles, which is closest to the position where the fluid is converted into the fluid droplets.

(2)

The microparticle sorting device according to (1), wherein the controller controls the driving voltage such that a distance from the position, where the fluid is converted into the fluid droplets, to the satellite fluid droplet and/or a state of a constricted region of the fluid right before being converted into the fluid droplets become constant.

(3)

The microparticle sorting device according to (2), wherein the controller controls the driving voltage such that a width of the constricted region becomes constant.

(4)

The microparticle sorting device according to (1), wherein the controller controls the driving voltage such that a distance from the position, where the fluid is converted into the fluid droplets, to a narrowest part of the constricted region of the fluid right before being converted into the fluid droplets becomes constant.

(5)

The microparticle sorting device according to any one of (1) to (4), wherein the controller controls the position of the imaging element such that the position, in the image, where the fluid is converted into the fluid droplets becomes constant.

(6)

The microparticle sorting device according to (5), wherein the controller calculates a distance from an upper end of the image to the position where the fluid is converted into the fluid droplets, and controls the position of the imaging element such that the distance becomes constant.

(7)

The microparticle sorting device according to any one of (1) to (6), including:

a sheath liquid storage tank configured to store sheath liquid included in the fluid stream;

a first water depth detector configured to detect a water depth of the sheath liquid stored in the sheath liquid storage tank;

a first pressure detector configured to detect air pressure inside the sheath liquid storage tank; and a first pressure controller configured to control the air pressure inside the sheath liquid storage tank such that a sum of the fluid pressure which is calculated from the water depth detected by the first water depth detector and the air pressure detected by the first pressure detector becomes constant.

(8)

The microparticle sorting device according to any one of (1) to (7), including:

a sample liquid storage tank configured to store sample liquid including microparticles and included in the fluid stream;

a second water depth detector configured to detect a water depth of the sample liquid stored in the sample liquid storage tank;

a second pressure detector configured to detect air pressure inside the sample liquid storage tank; and a second pressure controller configured to control the air pressure inside the sample liquid storage tank such that a sum of the fluid pressure which is calculated from the water depth detected by the second water depth detector and the air pressure detected by the second pressure detector becomes constant.

(9)

A method for sorting microparticles, including:

controlling driving voltage of an oscillation element which gives oscillation to an orifice and/or a position of an imaging element that obtains an image based on a state of fluid in the image taken at a position where the fluid discharged from the orifice which generates a fluid stream is converted into fluid droplets and/or a state of a satellite fluid droplet which does not include microparticles and exists between the position, where the fluid is converted into the fluid droplets, and a fluid droplet, among the fluid droplets including the microparticles, which is closest to the position where the fluid is converted into the fluid droplets.

(10)

The method for sorting microparticles according to (9), wherein the driving voltage is controlled such that a distance from the position, where the fluid is converted into the fluid droplets, to the satellite fluid droplet and/or a state of a constricted region of the fluid right before being converted into the fluid droplets become constant.

(11)

The method for sorting microparticles according to (10), wherein the driving voltage is controlled such that a width of the constricted region becomes constant.

(12)

The method for sorting microparticles according to (9), wherein the driving voltage is controlled such that a distance from the position, where the fluid is converted into the fluid droplets, to a narrowest part of the constricted region of the fluid right before being converted into the fluid droplets becomes constant.

(13)

The method for sorting microparticles according to any one of (9) to (12), wherein the position of the imaging element is controlled such that the position, in the image, where the fluid is converted into the fluid droplets becomes constant.

(14)

The method for sorting microparticles according to (13), wherein a distance from an upper end of the image to the position where the fluid is converted into the fluid droplets is calculated, and the position of the imaging element is controlled such that the distance becomes constant.

(15)

A program which causes a controller of a microparticle sorting device to execute a function of controlling driving voltage of an oscillation element which gives oscillation to an orifice and/or a position of an imaging element which obtains an image, based on a state of fluid in the image taken at a position where the fluid discharged from the orifice which generates a fluid stream is converted into fluid droplets and/or a state of a satellite fluid droplet which does not include microparticles and exists between the position, where the fluid is converted into the fluid droplets, and a fluid droplet, among the fluid droplets including the microparticles, which is closest to the position where the fluid is converted into the fluid droplets.

REFERENCE SIGNS LIST 1 microparticle sorting device
2 microchip
3 oscillation element
4 electrode for charging
5a, 5b deflection plate
6a to 6c recovery container
7 imaging element (camera)
8 controller
10 sheath container
11 scale
12, 17 air pressure sensor
13, 18 compressor
14 pressure controller
15 sample container
16 camera
21 orifice
22 sample inlet
23 sheath inlet
24 suction outlet
31 voltage supplier
70 position adjustment mechanism
71 to 73 image
221 sample liquid
231 sheath liquid
BP break-off point
D fluid droplet
S fluid stream
SD satellite fluid droplet
FD fluid droplet inside liquid column
L liquid column length
m final fluid droplet length in liquid column
w liquid column constricted width

The invention claimed is:

1. A microparticle sorting device, comprising:
an imaging element configured to obtain an image of at least one part of a fluid stream including a fluid, fluid droplets and a first satellite fluid droplet which does not include microparticles; and
a controller configured to control a driving voltage of an oscillation element which gives oscillation to an orifice and to control a position of the imaging element, based on comparing a first distance, determined from the image, from a break-off point where the fluid is converted into the fluid droplets to the first satellite fluid droplet, with a second distance determined from a reference image.

2. A microparticle sorting method comprising:
obtaining, by an imaging element, an image of at least one part of a fluid stream including a fluid, fluid droplets and a first satellite fluid droplet which does not include microparticles; and
controlling, by a controller, a driving voltage of an oscillation element which causes oscillation of an orifice and controlling a position of the imaging element, based on comparing a first distance, determined from the image, from a break-off point where the fluid is converted into the fluid droplets to the first satellite fluid droplet, with a second distance determined from a reference image.

\* \* \* \* \*